(12) United States Patent
Smiley et al.

(10) Patent No.: US 12,167,959 B2
(45) Date of Patent: Dec. 17, 2024

(54) ADJUSTABLE INTRAOCULAR LENSES AND METHODS OF POST-OPERATIVELY ADJUSTING INTRAOCULAR LENSES

(71) Applicant: Alcon Inc., Fribourg (CH)

(72) Inventors: Terah Whiting Smiley, Davis, CA (US); Andrew R. Walz, Longmont, CO (US); Sharad Hajela, San Carlos, CA (US); Gregory Vinton Matthews, San Francisco, CA (US); Robert Demitri Angelopoulos, San Jose, CA (US); Nathan Lewis, San Jose, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/302,298

(22) Filed: Apr. 18, 2023

(65) Prior Publication Data

US 2023/0248509 A1    Aug. 10, 2023

Related U.S. Application Data

(62) Division of application No. 17/060,901, filed on Oct. 1, 2020, now Pat. No. 11,660,182.
(Continued)

(51) Int. Cl.
*A61F 2/16* (2006.01)
*A61L 27/44* (2006.01)
*A61L 27/50* (2006.01)

(52) U.S. Cl.
CPC .......... *A61F 2/1624* (2013.01); *A61F 2/1605* (2015.04); *A61F 2/1635* (2013.01);
(Continued)

(58) Field of Classification Search
CPC .... A61F 2/1613; A61F 2/1624; A61F 2/1635; A61F 2/1648; A61F 2/1659;
(Continued)

(56) References Cited

U.S. PATENT DOCUMENTS

| | | |
|---|---|---|
| 4,111,995 A | 9/1978 | Nelson |
| 4,251,887 A | 2/1981 | Anis |

(Continued)

FOREIGN PATENT DOCUMENTS

| | | |
|---|---|---|
| CN | 1283974 | 2/2001 |
| CN | 1367667 | 9/2002 |

(Continued)

OTHER PUBLICATIONS

Baughman et al. "Negative poisson's ratios for extreme states fo matter," *Science*, vol. 288, pp. 2018-2022, Jun. 16, 2000.
(Continued)

*Primary Examiner* — Javier G Blanco
(74) *Attorney, Agent, or Firm* — Levine Bagade Han LLP

(57) ABSTRACT

Disclosed are adjustable accommodating intraocular lenses and methods of adjusting accommodating intraocular lenses post-operatively. In one embodiment, an adjustable accommodating intraocular lens comprises an optic portion and a peripheral portion. At least one of the optic portion and the peripheral portion can be made in part of a composite material comprising an energy absorbing constituent and a plurality of expandable components. At least one of a base power and a cylindricity of the optic portion can be configured to change in response to an external energy directed at the composite material.

16 Claims, 11 Drawing Sheets

Related U.S. Application Data

(60) Provisional application No. 62/911,039, filed on Oct. 4, 2019.

(52) U.S. Cl.
CPC ............ *A61F 2/1659* (2013.01); *A61L 27/44* (2013.01); *A61L 27/443* (2013.01); *A61L 27/50* (2013.01); *A61F 2002/1681* (2013.01); *A61F 2002/169* (2015.04); *A61F 2002/16901* (2015.04); *A61F 2230/0069* (2013.01); *A61F 2250/0003* (2013.01); *A61L 2300/204* (2013.01); *A61L 2300/442* (2013.01); *A61L 2430/16* (2013.01)

(58) Field of Classification Search
CPC .... A61F 2002/16901; A61F 2210/0047; A61F 2250/0003; A61F 2250/0013; A61L 2300/442; A61L 2430/16
See application file for complete search history.

(56) References Cited

U.S. PATENT DOCUMENTS

| | | |
|---|---|---|
| 4,253,199 A | 3/1981 | Banko |
| 4,254,509 A | 3/1981 | Tennant |
| 4,258,311 A | 3/1981 | Tokuda et al. |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,855 A | 3/1984 | Pannu |
| 4,435,856 A | 3/1984 | L'esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | Mcclure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,764,423 A | 8/1988 | Yamaguchi et al. |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turley |
| 4,902,293 A | 2/1990 | Feaster |
| 4,913,536 A | 4/1990 | Barnea |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,078,740 A | 1/1992 | Walman |
| 5,145,884 A | 9/1992 | Yamamoto et al. |
| 5,145,935 A | 9/1992 | Hayashi |
| 5,152,789 A | 10/1992 | Willis |
| 5,169,920 A | 12/1992 | Okawa |
| 5,171,266 A | 12/1992 | Wiley et al. |
| 5,200,430 A | 4/1993 | Federman |
| 5,201,763 A | 4/1993 | Brady et al. |
| 5,203,788 A | 4/1993 | Wiley |
| 5,213,579 A | 5/1993 | Yamada et al. |
| 5,217,491 A | 6/1993 | Vanderbilt |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |
| 5,275,624 A | 1/1994 | Hara et al. |
| 5,288,293 A | 2/1994 | O'donnell |
| 5,290,892 A | 3/1994 | Namdaran et al. |
| 5,326,347 A | 7/1994 | Cumming |
| 5,391,590 A | 2/1995 | Gerace et al. |
| 5,405,386 A | 4/1995 | Rheinish et al. |
| 5,426,166 A | 6/1995 | Usifer et al. |
| 5,443,506 A | 8/1995 | Garabet |
| 5,444,106 A | 8/1995 | Zhou et al. |
| 5,444,135 A | 8/1995 | Cheradame et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,567,365 A | 10/1996 | Weinschenk et al. |
| 5,578,081 A | 11/1996 | Mcdonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,633,504 A | 5/1997 | Collins et al. |
| 5,665,822 A | 9/1997 | Bitler et al. |
| 5,674,282 A | 10/1997 | Cumming |
| 5,676,669 A | 10/1997 | Colvard |
| 5,693,095 A | 12/1997 | Freeman et al. |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | Mcdonald |
| 5,800,533 A | 9/1998 | Eggleston et al. |
| 5,843,188 A | 12/1998 | Mcdonald |
| 5,891,931 A | 4/1999 | Leboeuf et al. |
| 5,928,282 A | 7/1999 | Nigam |
| 5,964,802 A | 10/1999 | Anello et al. |
| 5,968,095 A | 10/1999 | Norrby |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,229,641 B1 | 5/2001 | Kosaka |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,348,437 B1 | 2/2002 | Avery et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |

(56) References Cited

U.S. PATENT DOCUMENTS

| | | |
|---|---|---|
| 6,423,094 B1 | 7/2002 | Sarfarazi |
| 6,436,092 B1 | 8/2002 | Peyman |
| 6,443,985 B1 | 9/2002 | Woods |
| 6,450,642 B1 | 9/2002 | Jethmalani et al. |
| 6,464,725 B2 | 10/2002 | Skotton |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,528,602 B1 | 3/2003 | Freeman et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,914,247 B2 | 7/2005 | Duggan et al. |
| 6,926,736 B2 | 8/2005 | Peng et al. |
| 6,935,743 B2 | 8/2005 | Shadduck |
| 6,949,093 B1 | 9/2005 | Peyman |
| 6,966,649 B2 | 11/2005 | Shadduck |
| 6,969,403 B2 | 11/2005 | Peng et al. |
| 7,001,374 B2 | 2/2006 | Peyman |
| 7,060,094 B2 | 6/2006 | Shahinpoor et al. |
| 7,068,439 B2 | 6/2006 | Esch et al. |
| 7,070,276 B2 | 7/2006 | Koretz |
| 7,074,227 B2 | 7/2006 | Portney |
| 7,122,053 B2 | 10/2006 | Esch |
| 7,144,423 B2 | 12/2006 | Mcdonald |
| 7,217,288 B2 | 5/2007 | Esch et al. |
| 7,241,312 B2 | 7/2007 | Lai et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,311,194 B2 | 12/2007 | Jin et al. |
| 7,438,723 B2 | 10/2008 | Esch |
| 7,485,144 B2 | 2/2009 | Esch |
| 7,494,505 B2 | 2/2009 | Kappelhof et al. |
| 7,637,947 B2 | 12/2009 | Smith et al. |
| 7,763,069 B2 | 7/2010 | Brady et al. |
| 7,776,088 B2 | 8/2010 | Shadduck |
| 7,988,292 B2 | 8/2011 | Neal et al. |
| 8,048,155 B2 | 11/2011 | Shadduck |
| 8,158,712 B2 | 4/2012 | Your |
| 8,162,927 B2 | 4/2012 | Peyman |
| 8,303,656 B2 | 11/2012 | Shadduck |
| 8,314,927 B2 | 11/2012 | Choi et al. |
| 8,328,869 B2 | 12/2012 | Smiley et al. |
| 8,361,145 B2 | 1/2013 | Scholl et al. |
| 8,425,599 B2 | 4/2013 | Shadduck |
| 8,447,086 B2 | 5/2013 | Hildebrand et al. |
| 8,454,688 B2 | 6/2013 | Esch et al. |
| 8,662,663 B2 | 3/2014 | Matsushita et al. |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,044,317 B2 | 6/2015 | Hildebrand et al. |
| 9,277,987 B2 | 3/2016 | Smiley et al. |
| 9,456,895 B2 | 10/2016 | Shadduck |
| 9,693,858 B2 | 7/2017 | Hildebrand et al. |
| 9,855,139 B2 | 1/2018 | Matthews et al. |
| 10,042,183 B2 | 8/2018 | Goodenough et al. |
| 10,076,858 B2 | 9/2018 | Gerardi et al. |
| 10,159,566 B2 | 12/2018 | Hadba et al. |
| 10,195,020 B2 | 2/2019 | Matthews |
| 10,299,913 B2 | 5/2019 | Smiley et al. |
| 10,350,060 B2 | 7/2019 | Smiley et al. |
| 10,433,949 B2 | 10/2019 | Smiley et al. |
| 10,433,950 B2 | 10/2019 | Shadduck |
| 10,534,113 B2 | 1/2020 | Shadduck |
| 10,595,989 B2 | 3/2020 | Hildebrand et al. |
| 11,426,270 B2 | 8/2022 | Hildebrand et al. |
| 11,471,272 B2 | 10/2022 | Smiley |
| 11,660,182 B2 | 5/2023 | Smiley et al. |
| 2001/0001836 A1 | 5/2001 | Cumming |
| 2001/0016771 A1 | 8/2001 | Cumming |
| 2001/0039449 A1 | 11/2001 | Johnson et al. |
| 2001/0051826 A1 | 12/2001 | Bogaert et al. |
| 2002/0016629 A1 | 2/2002 | Sandstedt et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0188351 A1 | 12/2002 | Laguette |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0147046 A1 | 8/2003 | Shadduck |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |

(56) References Cited

U.S. PATENT DOCUMENTS

| | | |
|---|---|---|
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | Mcnicholas |
| 2004/0054408 A1 | 3/2004 | Glick et al. |
| 2004/0059343 A1 | 3/2004 | Shearer et al. |
| 2004/0066489 A1 | 4/2004 | Benedikt et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0085515 A1 | 5/2004 | Roffman et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0230203 A1 | 11/2004 | Yaguchi |
| 2005/0021139 A1 | 1/2005 | Shadduck |
| 2005/0090612 A1 | 4/2005 | Soane et al. |
| 2005/0113911 A1 | 5/2005 | Peyman |
| 2005/0119740 A1 | 6/2005 | Esch et al. |
| 2005/0125000 A1 | 6/2005 | Tourrette et al. |
| 2005/0131535 A1 | 6/2005 | Woods |
| 2005/0146685 A1 | 7/2005 | Hanaki et al. |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0061729 A1 | 3/2006 | Shadduck |
| 2006/0069433 A1 | 3/2006 | Nun |
| 2006/0158611 A1 | 7/2006 | Piers et al. |
| 2006/0246112 A1 | 11/2006 | Snyder et al. |
| 2006/0253196 A1 | 11/2006 | Woods |
| 2007/0010880 A1 | 1/2007 | Esch |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0203578 A1 | 8/2007 | Scholl et al. |
| 2007/0213817 A1 | 9/2007 | Esch et al. |
| 2007/0260308 A1 | 11/2007 | Tran |
| 2007/0299487 A1 | 12/2007 | Shadduck |
| 2008/0015689 A1 | 1/2008 | Esch et al. |
| 2008/0046074 A1 | 2/2008 | Smith et al. |
| 2008/0046075 A1 | 2/2008 | Esch et al. |
| 2008/0306587 A1 | 12/2008 | Your |
| 2009/0005865 A1 | 1/2009 | Smiley et al. |
| 2009/0030425 A1 | 1/2009 | Smiley et al. |
| 2009/0079940 A1 | 3/2009 | Dai et al. |
| 2009/0149952 A1 | 6/2009 | Shadduck |
| 2009/0155371 A1 | 6/2009 | Sojka et al. |
| 2009/0312836 A1 | 12/2009 | Pinchuk et al. |
| 2010/0016965 A1 | 1/2010 | Hong et al. |
| 2010/0131058 A1 | 5/2010 | Shadduck |
| 2010/0179653 A1 | 7/2010 | Argento et al. |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0052020 A1 | 3/2011 | Hildebrand et al. |
| 2011/0208301 A1 | 8/2011 | Anvar et al. |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2012/0022547 A1 | 1/2012 | Hildebrand et al. |
| 2012/0078361 A1 | 3/2012 | Shadduck |
| 2012/0226351 A1 | 9/2012 | Peyman |
| 2012/0245591 A1 | 9/2012 | Matthews |
| 2013/0060331 A1 | 3/2013 | Shadduck |
| 2013/0103146 A1 | 4/2013 | Smiley et al. |
| 2013/0131794 A1 | 5/2013 | Smiley et al. |
| 2013/0250239 A1 | 9/2013 | Hildebrand et al. |
| 2013/0268070 A1 | 10/2013 | Esch et al. |
| 2014/0249625 A1 | 9/2014 | Shadduck |
| 2015/0057642 A1 | 2/2015 | Zickler et al. |
| 2015/0087743 A1 | 3/2015 | Anvar et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0038278 A1 | 2/2016 | Matthews |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2017/0020662 A1 | 1/2017 | Shadduck |
| 2017/0049561 A1 | 2/2017 | Smiley et al. |
| 2017/0079773 A1 | 3/2017 | Matthews et al. |
| 2017/0281334 A1 | 10/2017 | Zhao |
| 2017/0290658 A1 | 10/2017 | Hildebrand et al. |
| 2018/0085213 A1 | 3/2018 | Hadba et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0177589 A1 | 6/2018 | Argento et al. |
| 2018/0256315 A1 | 9/2018 | Hildebrand et al. |
| 2019/0053892 A1 | 2/2019 | Siney et al. |
| 2019/0076243 A1 | 3/2019 | Hadba et al. |
| 2019/0361231 A1 | 11/2019 | Kurz |
| 2019/0374333 A1 | 12/2019 | Shadduck |
| 2020/0332085 A1 | 10/2020 | Ebe et al. |
| 2020/0337833 A1 | 10/2020 | Green |
| 2020/0405541 A1 | 12/2020 | Raksi |
| 2021/0100649 A1 | 4/2021 | Smiley |
| 2021/0100650 A1 | 4/2021 | Smiley et al. |
| 2021/0291469 A1 | 9/2021 | Zheng et al. |
| 2022/0313080 A1 | 10/2022 | Hernandez et al. |
| 2022/0409363 A1 | 12/2022 | Smiley |
| 2023/0191730 A1 | 6/2023 | Walz et al. |
| 2023/0240836 A1 | 8/2023 | Irby et al. |
| 2024/0148554 A1 | 5/2024 | Paliwal et al. |

FOREIGN PATENT DOCUMENTS

| | | |
|---|---|---|
| CN | 1378440 | 11/2002 |
| CN | 1384727 | 12/2002 |
| EP | 0898972 | 3/1999 |
| FR | 2655841 | 6/1991 |
| FR | 2784575 | 12/2000 |
| JP | H05(1993)-171056 | 7/1993 |
| JP | 07-044938 | 5/1995 |
| JP | 08-501715 | 2/1996 |
| JP | 08-224295 | 9/1996 |
| JP | 09-294754 | 11/1997 |
| JP | 10-206609 | 8/1998 |
| JP | 11-047168 | 2/1999 |
| JP | 1999-047168 | 2/1999 |
| JP | 11-056998 | 3/1999 |
| JP | 11-169391 | 6/1999 |
| JP | 11-276509 | 10/1999 |
| JP | 11-332903 | 12/1999 |
| JP | 2000-250203 | 9/2000 |
| JP | 2001-502592 | 2/2001 |
| JP | 2003-144387 | 5/2003 |
| JP | 2003-524503 | 8/2003 |
| JP | 2003-530978 | 10/2003 |
| JP | 2006-523130 | 10/2006 |
| JP | 2007-513715 | 5/2007 |
| JP | 2007-516794 | 6/2007 |
| JP | 2007-518447 | 7/2007 |
| JP | 2010-095719 | 4/2010 |
| JP | 2016-138050 | 8/2016 |
| JP | 2017-148614 | 8/2017 |
| SU | 1810052 | 4/1993 |
| WO | WO 1995/002378 | 1/1995 |
| WO | WO 1997/006751 | 2/1997 |
| WO | WO 2000/041650 | 7/2000 |
| WO | WO 2000/064655 | 11/2000 |
| WO | WO 2001/060286 | 8/2001 |

(56) References Cited

FOREIGN PATENT DOCUMENTS

| WO | WO 2001/089435 | 11/2001 |
|---|---|---|
| WO | WO 2001/097742 | 12/2001 |
| WO | WO 2002/051338 | 7/2002 |
| WO | WO 2004/010895 | 2/2004 |
| WO | WO 2004/046768 | 6/2004 |
| WO | WO 2004/072689 | 8/2004 |
| WO | WO 2004/081613 | 9/2004 |
| WO | WO 2005/018504 | 3/2005 |
| WO | WO 2005/084588 | 9/2005 |
| WO | WO 2009/015234 | 1/2009 |
| WO | WO 2018/222558 | 12/2018 |
| WO | WO 2018/227014 | 12/2018 |
| WO | WO 2021/067574 | 4/2021 |
| WO | WO 2021/067579 | 4/2021 |
| WO | WO 2022/216451 | 10/2022 |
| WO | WO 2023/122490 | 6/2023 |
| WO | WO 2023/147224 | 8/2023 |
| WO | WO 2024/102536 | 5/2024 |

OTHER PUBLICATIONS

Baughman, "Avoiding the shrink," *Nature*, vol. 425, p. 667, Oct. 16, 2003.

Conlisk, A. T. et al. "Mass Transfer and Flow in Electrically Charged Micro- and Nano-channels," *Analytical Chemistry*, vol. 74; iss. 9; pp. 2139-2150; May 2002.

Dubbelman et al. "The Thickness of the Aging Human Lens Obtained from Corrected Scheimpflug Images," *Optometry & Vision Science*; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Gordon, "Applications of shape memory polyurethanes," *Proceedings of the First Intl Conf. on Shape Memory and Superelastic Tech.*, Asilomar Conference Center, Pacific Grove, CA, USA, pp. 115-120, Mar. 1994.

Gruber et al. "Exhaustive soxhlet extraction for the complete removal of residual compounds," *Journal of Biomedical Materials Research*, vol. 53; No. 5; pp. 445-448; Mar. 2000.

Jeon et al., "Shape memory and nanostructure in poly(norbornyl-POSS) copolymers," *Polymer International*, vol. 49, pp. 453-457, May 2000.

Kim et al., "Polyurethanes having shape memory effects," *Polymer*, vol. 37, No. 26, pp. 5781-5793, Dec. 1996.

Lakes et al., "Dramatically stiffer elastic composite materials due to negative stiffness phase?," *Journal of the Mechanics and Physics of Solids*, vol. 50, pp. 979-1009, May 2002.

Lakes et al., "Extreme damping in composite materials with negative-stiffness inclusions," *Nature*, vol. 410, pp. 565-567, Mar. 29, 2001.

Lakes et al., "Microbuckling instability in elastomeric cellular sollids," *J. Materials Science*, vol. 28, pp. 4667-4672, Jan. 1993.

Lakes, "A broader view of membranes," *Nature*, vol. 414, pp. 503-504, Nov. 29, 2001.

Lakes, "Deformations in extreme matter," *Science*; perspectives; vol. 288; No. 5473; pp. 1976-1977; Jun. 16, 2000.

Lakes, "Extreme damping in compliant composites with a negative-stiffness phase," *Philosophical Magazine Letters*, vol. 81, No. 2, pp. 95-100, Feb. 2001.

Lakes, "Extreme damping in composite materials with a negative stiffness phase," *Physical Review Letters*, vol. 86, No. 13, pp. 2897-2900, Mar. 26, 2001.

Lakes, "Negative poisson's ratio materials," *Science*, vol. 238, p. 551, Oct. 23, 1987.

Lakes, "No contractile obligations," *Nature*, vol. 358, pp. 713-714, Dec. 31, 1992.

Lendlein et al., "Biodegradable, elastic shape-memory polymers for potential biomedical applications", *Science*; vol. 296; pp. 1673-1676; May 31, 2002.

Lendlein et al., "Shape-memory polymers," *Angew. Chem. Int. Ed.*; vol. 41; pp. 2034-2057; Jun. 2002.

Li et al., "Crystallinity and morphology of segmented polyurethanes with different soft-segment length," *Journal of Applied Polymer Science*, vol. 62, pp. 631-638, Oct. 1996.

Liu et al., "Thermomechanical characterization of a tailored series of shape memory polymers," *Journal of Applied Medical Polymers*, vol. 6, No. 2, Dec. 2002.

Mather et al., "Strain recovery in POSS hybrid thermoplastics," *Polymer Preprints*, vol. 41, No. 1, pp. 528-529, Feb. 2000.

Metcalfe et al., "Cold hibernated elastic memory foams for endovascular interventions," Biomaterials, vol. 24, pp. 491-497, Feb. 2003.

Takahashi et al., "Structure and properties of shape-memory polyurethane block copolymers," *Journal of Applied Polymer Science*, vol. 60, pp. 1061-1069, May 1996.

Tehrani et al. "Capsule measuring ring to predict capsular bag diameter and follow its course after foldable intraocular lens implantation," *J Cataract Refract Surg.*; vol. 29; No. 11; pp. 2127-2134; Nov. 29, 2003.

Tobushi et al., "Thermomechanical properties of shape memory polymers of polyurethane series and their applications," *Journal de Physique IV, Colloque C1*, vol. 6, pp. 377-384, Aug. 1996.

Vass et al. "Prediction of pseudophakic capsular bag diameter based on biometric variables," *J Cataract Refract Surg.*; vol. 25; pp. 1376-1381; Oct. 1999.

Wang et al., "Deformation of extreme viscoelastic metals and composites," *Materials Science and Enginerring A*, vol. 370, pp. 41-49, Apr. 15, 2004.

Wang et al., "Extreme stiffness systems due to negative stiffness elements," *American Journal of Physics*, vol. 72, No. 1, pp. 40-50, Jan. 2004.

Wyant et al; "Basic Wavefront Aberration Theory for Optical Metrology," *Applied Optics and Optical Engineering*, vol. XI, pp. 1, 28-39, Aug. 10, 1992.

Xu et al., "Making negative poisson's ratio microstructures by soft lithography," *Advanced Materials*, vol. 11, No. 14, pp. 1186-1189, Jun. 1999.

ADJUSTABLE INTRAOCULAR LENSES AND METHODS OF POST-OPERATIVELY ADJUSTING INTRAOCULAR LENSES

CROSS-REFERENCE TO RELATED APPLICATION

This application is a divisional of U.S. patent application Ser. No. 17/060,901 filed on Oct. 1, 2020, which claims the benefit of U.S. Provisional Application No. 62/911,039 filed on Oct. 4, 2019, the entirety of which is incorporated herein by reference.

TECHNICAL FIELD

The present disclosure relates generally to the field of intraocular lenses, and, more specifically, to adjustable intraocular lenses and methods of adjusting intraocular lenses

BACKGROUND

A cataract is a condition involving the clouding over of the normally clear lens of a patient's eye. Cataracts occur as a result of aging, hereditary factors, trauma, inflammation, metabolic disorders, or exposure to radiation. Age-related cataract is the most common type of cataracts. In treating a cataract, the surgeon removes the crystalline lens matrix from the patient's lens capsule and replaces it with an intraocular lens (IOL). Traditional IOLs provide one or more selected focal lengths that allow the patient to have distance vision. However, after cataract surgery, patients with traditional IOLs often require glasses or other corrective eyewear for certain activities since the eye can no longer undertake accommodation (or change its optical power) to maintain a clear image of an object or focus on an object as its distance varies.

Newer IOLs such as accommodating IOLs, allow the eye to regain at least some focusing ability. Accommodating IOLs (AIOLs) use forces available in the eye to change some portion of the optical system in order to refocus the eye on distant or near targets. Examples of AIOLs are discussed in the following U.S. patent publications: U.S. Pat. Pub. No. 2018/0256315; U.S. Pat. Pub. No. 2018/0153682; and U.S. Pat. Pub. No. 2017/0049561 and in the following issued U.S. Pat. Nos. 10,299,913; 10,195,020; and 8,968,396, the contents of which are incorporated herein by reference in their entireties.

Even with AIOLs, there may be a need to adjust such lenses post-operatively or after implantation within the eye of a patient. For example, once an AIOL is implanted within the capsular bag, an aggressive healing response by tissue within the capsular bag can squeeze an AIOL and drive the optical power higher than initially anticipated. In some cases, the pre-operative biometry measurements made on a patient's eye may be incorrect, leading to IOLs with the wrong lens power being prescribed and implanted within the patient. Moreover, a patient's cornea or muscles within the eye may change as a result of injury, disease, or aging. In such cases, it may also be necessary to adjust the patient's implanted IOLs or AIOLs to account for such changes.

Besides lower-order aberrations (such as focusing power), higher-order aberrations such as cylindrical astigmatism and spherical aberration are also commonly corrected with intraocular lenses. Cylindrical astigmatism is generally developed in the cornea naturally and a large proportion of patients with preexisting cataracts also have some degree of astigmatism. While toric IOLs have been used to correct astigmatism at the time of cataract surgery, one difficulty faced by all toric lens makers is that such lenses are rotationally asymmetric so proper placement of the lens relative to a patient's own existing aberration is crucial. When a misplacement does occur, a patient's only recourse is often to undergo additional surgery to correct for such a misplacement.

Therefore, a solution is needed which allows for post-implant adjustment of IOLs or AIOLs without having to undergo additional surgery. Such a solution should not overly complicate the design of such lenses and still allow the lenses to be cost-effectively manufactured.

SUMMARY

Disclosed herein are adjustable intraocular lenses, adjustable accommodating intraocular lenses, and methods of adjusting intraocular lenses and accommodating intraocular lenses. In one embodiment, an adjustable accommodating intraocular lens is disclosed comprising an optic portion comprising an anterior element and a posterior element. The anterior element can comprise an anterior optical surface. The posterior element can comprise a posterior optical surface. A fluid-filled optic fluid chamber can be defined in between the anterior element and the posterior element.

The optic portion can have a base power or base spherical power. The base power of the optic portion can be configured to change based on an internal fluid pressure within the fluid-filled optic fluid chamber. The base power of the optic portion can be configured to increase or decrease as fluid enters or exits the optic fluid chamber. The optic portion can be configured to change shape in response to fluid entering or exiting the optic fluid chamber. In certain embodiments, the anterior element of the optic portion can be configured to change shape in response to the fluid entering or exiting the optic fluid chamber. In other embodiments, the posterior element of the optic portion can be configured to change shape in response to the fluid entering or exiting the optic fluid chamber. In further embodiments, both the anterior element and the posterior element of the optic portion can be configured to change shape in response to the fluid entering or exiting the optic fluid chamber.

The base power of the optic portion can be configured to change in response to the shape change undertaken by the shape-changing optic portion (e.g., the anterior element, the posterior element, or a combination thereof). The shape-changing optic portion can be configured to change shape in response to a physiologic muscle movement (e.g., ciliary muscle movement) undertaken by a patient when the adjustable accommodating intraocular lens is implanted within an eye of the patient.

In some embodiments, the adjustable accommodating intraocular lens can comprise one or more haptics coupled to and extending from the optic portion. Each of the one or more haptics can comprise a haptic fluid chamber within the haptic. The base power of the optic portion can be configured to increase as fluid enters the optic fluid chamber from the haptic fluid chamber(s). The base power of the optic portion can be configured to decrease as fluid exits or is drawn out of the optic fluid chamber into the haptic fluid chamber(s).

The optic fluid chamber can be in fluid communication with or fluidly connected to the haptic fluid chamber(s). The optic fluid chamber can be in fluid communication with a haptic fluid chamber through a pair of fluid channels. The fluid channels can be conduits or passageways fluidly connecting the optic fluid chamber to the haptic fluid chamber. The pair of fluid channels can be spaced apart from one another. For example, the pair of fluid channels can be spaced apart between about 0.1 mm to about 1.0 mm.

In some embodiments, the pair of fluid channels can be defined and extend through part of the optic portion. More specifically, the pair of fluid channels can be defined and extend through the posterior element.

The one or more haptics can be coupled to the optic portion at a haptic-optic interface. The one or more haptics can be coupled to the optic portion at a reinforced portion along the optic portion. The reinforced portion can be part of the haptic-optic interface. The pair of fluid channels can be defined or formed within part of the reinforced portion.

In some embodiments, the adjustable accommodating intraocular lens can comprise two haptics coupled to and extending from the optic portion. The first haptic can comprise a first haptic fluid chamber within the first haptic. The second haptic can comprise a second haptic fluid chamber within the second haptic. The first haptic can be coupled to the optic portion at a first haptic-optic interface and the second haptic can be coupled to the optic portion at a second haptic-optic interface.

In these embodiments, the optic fluid chamber can be in fluid communication with both the first haptic fluid chamber and the second haptic fluid chamber. The optic fluid chamber can be in fluid communication with the first haptic fluid chamber through a first pair of fluid channels. The optic fluid chamber can be in fluid communication with the second haptic fluid chamber through a second pair of fluid channels.

The first pair of fluid channels can be spaced apart from one another. The first pair of fluid channels can be spaced apart between about 0.1 mm to about 1.0 mm. The second pair of fluid channels can be spaced apart from one another. The second pair of fluid channels can be spaced apart between about 0.1 mm to about 1.0 mm.

The first pair of fluid channels and the second pair of fluid channels can be defined and extend through part of the optic portion. The first pair of fluid channels and the second pair of fluid channels can be defined and extend through the posterior element.

The optic portion can also comprise a first reinforced portion and a second reinforced portion substantially on opposing sides of the optic portion or substantially diametrically opposed to one another. The first pair of fluid channels can be defined or formed within the first reinforced portion. The second pair of fluid channels can be defined or formed within the second reinforced portion.

The first pair of fluid channels can terminate at a first pair of apertures defined within the optic portion. The first pair of fluid channels can terminate at a first pair of apertures defined within the posterior element. The first pair of apertures can be spaced apart between about 0.1 mm to about 1.0 mm. The second pair of fluid channels can terminate at a second pair of apertures defined within the optic portion. The second pair of fluid channels can terminate at a second pair of apertures within the posterior element. The second pair of apertures can be spaced apart between about 0.1 mm to about 1.0 mm.

In some embodiments, the first pair of fluid channels and the second pair of fluid channels can be positioned substantially on opposite sides of the optic portion. The first pair of fluid channels can be positioned substantially diametrically opposed to the second pair of fluid channels.

In these embodiments, the first pair of apertures and the second pair of apertures can be positioned substantially on opposite sides of the optic portion. The first pair of apertures can be positioned substantially diametrically opposed to the second pair of apertures.

In some embodiments, at least one of the optic portion and the peripheral portion (e.g., the haptics) can be made in part of a cross-linked copolymer comprising a copolymer blend. Moreover, at least one of the optic portion and the peripheral portion can be made in part of a composite material comprising an energy absorbing constituent, a plurality of expandable components, and a composite base material made in part of the copolymer blend. At least one of a base power and a cylindricity of the optic portion can be configured to change in response to an external energy directed at the composite material.

In certain embodiments, the adjustable accommodating intraocular lens can be implanted within an eye of a subject. At least one of the base power and the cylindricity of the optic portion can be configured to change in response to the external energy directed at the composite material when the adjustable accommodating intraocular lens is implanted within an eye of the subject.

In some embodiments, the expandable components can be expandable microspheres comprising a blowing agent within expandable thermoplastic shells. The blowing agent can be a branched-chain hydrocarbon. For example, the branched-chain hydrocarbon can be isopentane.

The thickness of the thermoplastic shells can be configured to change in response to the external energy directed at the composite material. In some embodiments, the thermoplastic shells can be made in part of an acrylonitrile copolymer.

A diameter of at least one of the expandable microspheres can be configured to increase between about two times (2×) to about four times (4×) in response to the external energy directed at the composite material. A volume of at least one of the expandable microspheres can be configured to expand between about ten times (10×) to about fifty times (50×) in response to the external energy directed at the composite material.

The expandable components can comprise between about 5% to about 15% (more specifically, about 8% to about 12%) by weight of the composite material. For example, the expandable components can comprise about 10% by weight of the composite material.

The energy absorbing constituent can comprise between about 0.025% to about 1.0% (or, more specifically, about 0.045% to about 0.45%) by weight of the composite material. In some embodiments, the energy absorbing constituent can be an energy absorbing colorant. For example, a color of the energy absorbing colorant can be visually perceptible to a clinician or another medical professional when the accommodating intraocular lens is implanted within an eye.

The energy absorbing colorant can be a dye. For example, the dye can be an azo dye. In some embodiments, the dye can be a red azo dye such as Disperse Red 1 dye. The energy absorbing colorant can also comprise a pigment. For example, the pigment can be graphitized carbon black.

In some embodiments, at least one of the optic portion and the peripheral portion can be made in part of a first composite material and a second composite material. The first composite material can comprise a first energy absorbing colorant. The second composite material can comprise a second energy absorbing colorant. In certain embodiments, the color of the first energy absorbing colorant can be different from the color of the second energy absorbing colorant.

In addition to the copolymer blend, the composite base material can further comprise at least one of one or more reactive acrylic monomer diluents, a photoinitiator, and a thermal initiator. The copolymer blend can comprise an alkyl acrylate, a fluoro-alkyl acrylate, and a phenyl-alkyl acrylate. The composite material can remain relatively fixed at one or more locations within the optic portion or the peripheral portion during all phases of accommodation or disaccommodation of the intraocular lens.

As previously discussed, the base power of the adjustable accommodating intraocular lens can be configured to change in response to an external energy directed at a composite material making up at least part of the adjustable accommodating intraocular lens. The base power of the optic portion can be configured to change between about ±0.05 D to about ±0.5 D (e.g., more specifically, between about ±0.1 D to about ±0.2 D) in response to pulses of the external energy directed at the composite material. In some embodiments, the base power of the optic portion can be configured to change by up to ±2.0 D in total. In other embodiments, the base power of the optic portion can be configured to change by up to ±5.0 D in total.

In some embodiments, the external energy can be light energy. The external energy can be light energy from a laser light. The light energy can have a wavelength between about 488 nm to about 650 nm. For example, the light energy can be green laser light having a wavelength between about 520 nm to about 570 nm. As a more specific example, the light energy can be green laser light having a wavelength of about 532 nm.

The external energy directed or otherwise applied to the composite material can cause a persistent change in an optical parameter of the adjustable accommodating intraocular lens. For example, the external energy directed or otherwise applied to the composite material can cause a persistent change in the base power of the adjustable accommodating intraocular lens. Also, for example, the external energy directed or otherwise applied to the composite material can cause a persistent change in the cylindricity of the optic portion of the adjustable accommodating intraocular lens.

In some embodiments, the optic portion can be made in part of the composite material. In these embodiments, at least one of the base power and the cylindricity of the optic portion can be configured to change in response to the external energy directed at the optic portion. For example, the composite material can be located along a first peripheral edge of an anterior element of the optic portion. In this example, the composite material can also be located along a second peripheral edge diametrically opposed to the first peripheral edge. The cylindricity of the anterior optical surface can be configured to change in response to the external energy directed at the first peripheral edge and the second peripheral edge.

Alternatively, the composite material can also be located along a first peripheral edge along a second peripheral edge of a posterior element of the optic portion. The second peripheral edge can be diametrically opposed to the first peripheral edge. The cylindricity of the posterior optical surface can be configured to change in response to the external energy directed at the first peripheral edge and the second peripheral edge.

As previously discussed, the anterior element of the optic portion can be bonded or otherwise adhered circumferentially to the posterior element by an adhesive layer. In some embodiments, the adhesive layer can comprise the composite material. The base power of the optic portion can be configured to decrease in response to an external energy directed at the adhesive layer. The adhesive layer can be configured to expand in response to the external energy directed at the adhesive layer. Expansion of the adhesive layer can cause a volume of the optic fluid chamber within the optic portion to increase. An increase in the volume of the optic fluid chamber can cause an internal fluid pressure within the optic fluid chamber to decrease, thereby causing the anterior element to flatten or decrease its curvature.

In other embodiments, the peripheral portion (e.g., the haptic(s)) of the adjustable accommodating intraocular lens can be made in part of the composite material. As previously discussed, the peripheral portion can include at least one haptic comprising a fluid-filled haptic fluid chamber in fluid communication with the optic chamber. The base power of the optic portion can be configured to change in response to the external energy directed at portions of the peripheral portion made in part of the composite material. The external energy can cause fluid flow or fluid displacement between the fluid-filled optic chamber and the haptic fluid chamber.

For example, the base power can be configured to change in response to a change in the volume of the haptic fluid chamber. Also, for example, the base power of the adjustable accommodating intraocular lens can be configured to change in response to an interaction between the peripheral portion and a capsular environment surrounding the adjustable accommodating intraocular lens when the lens is implanted within an eye.

More specifically, the composite material can be configured or designed as a spacer extending radially from a haptic chamber wall. The spacer can be configured to expand in response to the external energy directed at the spacer. Expansion of the spacer can result in a reduction of the volume of the haptic fluid chamber by pushing the haptic(s) against one or more capsular bag walls.

The composite material can also be located partly within a haptic chamber wall surrounding the haptic fluid chamber. For example, the composite material can be located at least partially within a channel formed along a radially inner wall of the haptic. A volume of the haptic fluid chamber can be configured to increase in response to the external energy directed at the composite material.

In other embodiments, the composite material can be positioned or located at least partially along a radially outermost portion of a radially inner wall of the haptic. A volume of the haptic fluid chamber can be configured to decrease in response to the external energy directed at the composite material. In at least some of these embodiments, the composite material can expand into the haptic fluid chamber in response to the external energy directed at the composite material.

In further embodiments, a haptic of the adjustable accommodating intraocular lens can comprise a first haptic portion and a second haptic portion. The first haptic portion and the second haptic portion can be made in part of the composite material. A base power of the optic portion can be configured to increase in response to an external energy directed at the first haptic portion. For example, the base power of the optic portion can be configured to increase in response to fluid flowing from the haptic fluid chamber to the optic fluid chamber as a result of the external energy directed at the first haptic portion.

Moreover, the base power of the optic portion can be configured to decrease in response to the external energy directed at the second haptic portion. The base power of the optic portion can be configured to decrease in response to fluid flowing from the optic fluid chamber to the haptic fluid chamber as a result of the external energy directed at the second haptic portion. At least one of the first haptic portion and the second haptic portion can be located partly within a haptic chamber wall surrounding the haptic fluid chamber.

In some embodiments, the first haptic portion can be made in part of a first composite material and the second haptic portion can be made in part of a second composite material. The first composite material can comprise a first energy absorbing constituent and the second composite material can comprise a second energy absorbing constituent. The composition of the first energy absorbing constituent can be different from the composition of the second energy absorbing constituent. For example, the first energy absorbing constituent can be an energy absorbing dye having a first color. In this example, the second energy absorbing constituent can be another energy absorbing dye having a second color different from the first color.

The first haptic portion can be radially offset from the second haptic portion. In some embodiments, at least one of the first haptic portion and the second haptic portion can be oriented in a pattern such that a location of the at least one of the first haptic portion and the second haptic portion along the haptic is visually perceptible to a clinician or another medical professional.

A method of adjusting an accommodating intraocular lens is also disclosed. The method can comprise adjusting a base power of the accommodating intraocular lens by directing an external energy at a composite material within at least one of an optic portion and a peripheral portion of the accommodating intraocular lens. The composite material can comprise an energy absorbing constituent, a plurality of expandable components, and the composite base material made in part of the copolymer blend.

The method can further comprise adjusting the base power of the accommodating intraocular lens when the accommodating intraocular lens is implanted within an eye of a subject. The method can further comprise adjusting the cylindricity of an optical surface of the optic portion of the accommodating intraocular lens by directing an external energy at the composite material arranged at diametrically opposed peripheral edges of the optic portion.

The method can also comprise directing the external energy at the composite material to energize the energy absorbing constituent to cause thermal energy to be transferred to the expandable components. In some embodiments, the plurality of expandable components can be expandable microspheres comprising a blowing agent contained within thermoplastic shells. Directing the external energy at the composite material can cause the microspheres to expand.

In some embodiments, the external energy can be light energy. For example, the light energy can be laser light having a wavelength between about 488 nm to about 650 nm.

The method can further comprise adjusting the base power of the optic portion between about ±0.05 D to about ±0.5 D (e.g., more specifically, between about ±0.1 D to about ±0.2 D) in response to pulses of the external energy directed at the composite material.

The method can also comprise directing the external energy at the composite material to displace fluid between the optic chamber and the haptic fluid chamber. For example, the method can comprise directing the external energy at the composite material to change a volume of the haptic fluid chamber. This change in the volume of the haptic fluid chamber can result in a change in the base power of the accommodating intraocular lens. The method can further comprise adjusting the base power of the accommodating intraocular lens by directing the external energy at the composite material to cause a haptic of the lens to interact with a capsular environment surrounding the implanted accommodating intraocular lens.

Moreover, the method can also comprise adjusting the base power of the accommodating intraocular lens by directing the external energy at the composite material to change a volume of the optic fluid chamber. This change in the volume of the optic fluid chamber can result in fluid flow out of the optical fluid chamber, thereby causing part of the optic portion to change shape and the base power of the lens to decrease.

DETAILED DESCRIPTION

Figure 1A:
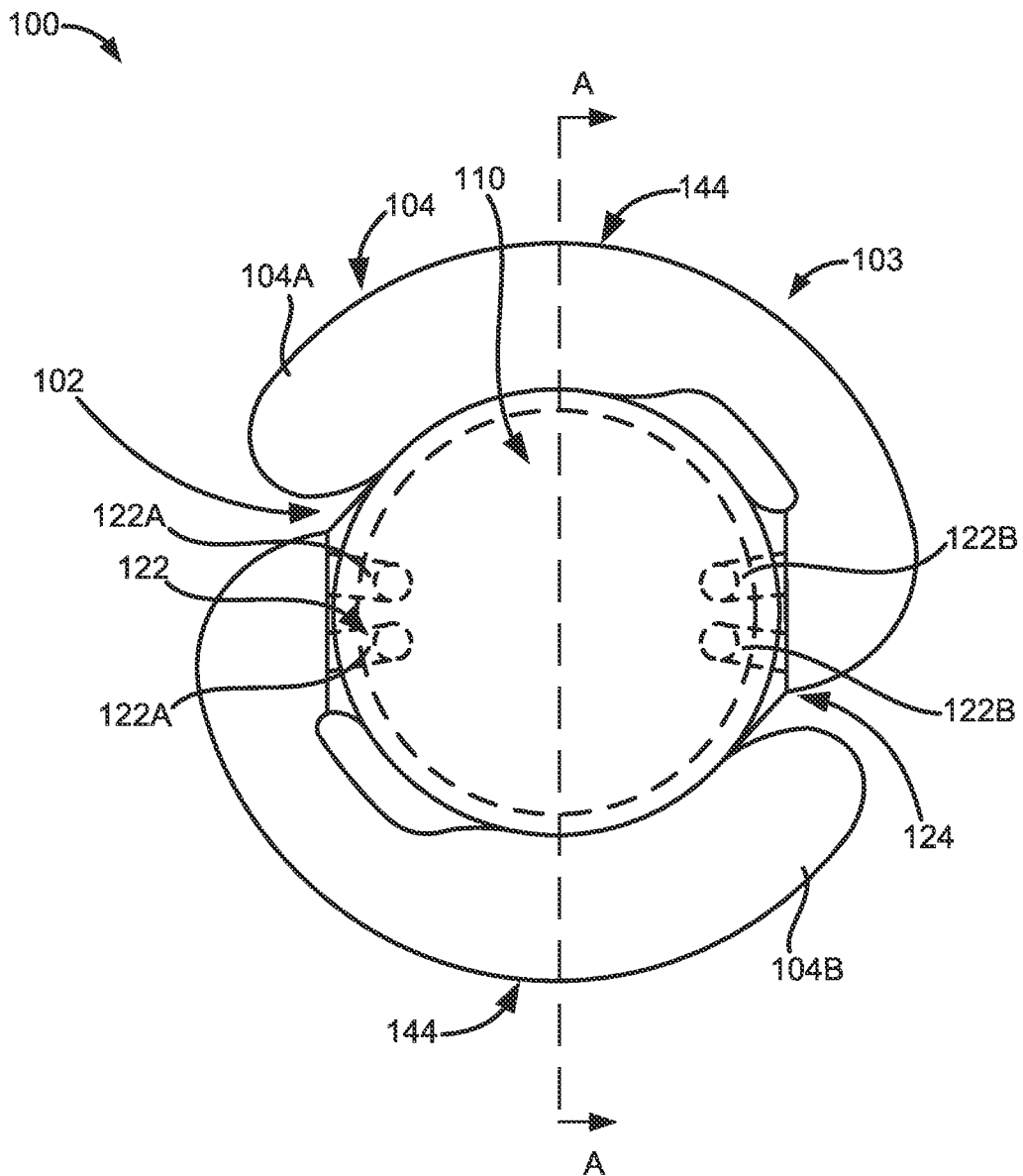
FIG. 1A illustrates a top plan view of an embodiment of an adjustable accommodating intraocular lens.

FIG. 1A illustrates a top plan view of an embodiment of an adjustable accommodating intraocular lens (AIOL) 100 for correcting defocus aberration, corneal astigmatism, spherical aberration, or a combination thereof. The adjustable AIOL 100 can comprise an optic portion 102 and a peripheral portion 103 that, in this embodiment, comprises one or more haptics 104 including a first haptic 104A and a second haptic 104B coupled to and extending peripherally from the optic portion 102. The adjustable AIOL 100 is configured to be positioned within a native capsular bag in which a native lens has been removed.

When implanted within the native capsular bag, the optic portion 102 can be adapted to refract light that enters the eye onto the retina. The peripheral portion 103 (e.g., the one or more haptics 104) can be configured to engage the capsular bag and is adapted to deform in response to ciliary muscle movement (e.g., muscle relaxation, muscle contraction, or a combination thereof) in connection with capsular bag reshaping. Engagement of the peripheral portion 103 (e.g., the one or more haptics 104) with the capsular bag will be discussed in more detail in the following sections.

Figure 1B:
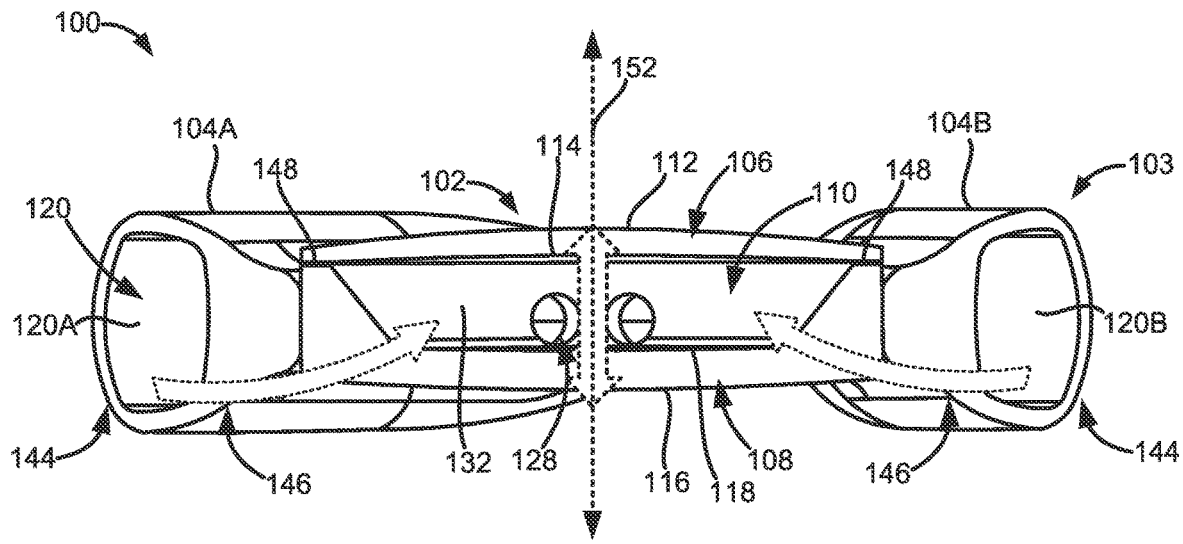
FIGS. 1B and 1C illustrate sectional views of an embodiment of the adjustable accommodating intraocular lens.
Figure 1C:
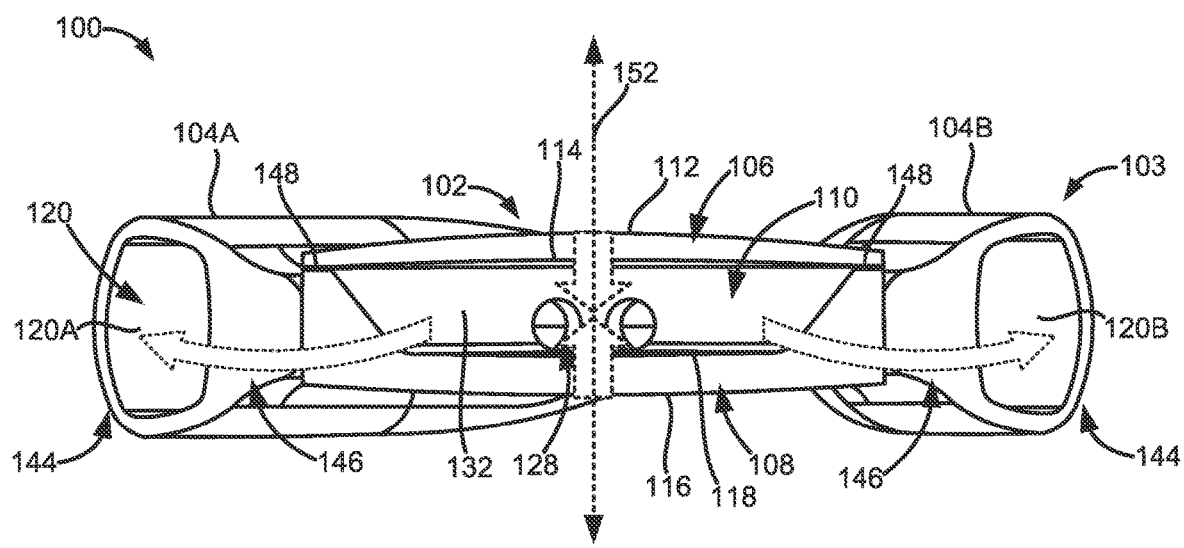

FIGS. 1B and 1C illustrate sectional views of an embodiment of the adjustable AIOL 100 as taken along cross-section A-A of FIG. 1A. As shown in FIGS. 1B and 1C, the optic portion 102 can comprise an anterior element 106 and a posterior element 108. A fluid-filled optic fluid chamber 110 can be defined in between the anterior element 106 and the posterior element 108.

The anterior element 106 can comprise an anterior optical surface 112 and an anterior inner surface 114 opposite the anterior optical surface 112. The posterior element 108 can comprise a posterior optical surface 116 and a posterior inner surface 118 opposite the posterior optical surface 116. Any of the anterior optical surface 112, the posterior optical surface 116, or a combination thereof can be considered and referred to as an external optical surface. The anterior inner surface 114 and the posterior inner surface 118 can face the optic fluid chamber 110. At least part of the anterior inner surface 114 and at least part of the posterior inner surface 118 can serve as chamber walls of the optic fluid chamber 110.

Each of the one or more haptics 104 can comprise a haptic fluid chamber 120 within the haptic 104. For example, the first haptic 104A can comprise a first haptic fluid chamber 120A within the first haptic 104A and the second haptic 104B can comprise a second haptic fluid chamber 120B within the second haptic 104B. The haptic fluid chamber 120 (e.g., any of the first haptic fluid chamber 120A, the second haptic fluid chamber 120B, or a combination thereof) can be in fluid communication with or fluidly connected to the optic fluid chamber 110.

The optic fluid chamber 110 can be in fluid communication with the one or more haptic fluid chambers 120 through a pair of fluid channels 122 (see FIG. 1A). The fluid channels 122 can be conduits or passageways fluidly connecting the optic fluid chamber 110 to the haptic fluid chamber 120. The pair of fluid channels 122 can be spaced apart from one another. For example, the pair of fluid channels 122 can be spaced apart between about 0.1 mm to about 1.0 mm. In some embodiments, each of the pair of fluid channels 122 has a diameter of between about 0.4 mm to about 0.6 mm.

In some embodiments, the pair of fluid channels 122 can be defined and extend through part of the optic portion 102. More specifically, the pair of fluid channels 122 can be defined and extend through the posterior element 108.

FIG. 1A illustrates that one or more haptics 104 of the peripheral portion 103 can be coupled to the optic portion 102 at a haptic-optic interface 124. For example, the one or more haptics 104 can be coupled to the optic portion at a reinforced portion 126 (see FIG. 1D) along the optic portion 102. The reinforced portion 126 can be part of the haptic-optic interface 124. The pair of fluid channels 122 can be defined or formed within part of the reinforced portion 126.

The optic fluid chamber 110 can be in fluid communication with the first haptic fluid chamber 120A through a first pair of fluid channels 122A. The optic fluid chamber 110 can also be in fluid communication with the second haptic fluid chamber 120B through a second pair of fluid channels 122B.

The two fluid channels of the first pair of fluid channels 122A can be spaced apart from one another. The two fluid channels of the first pair of fluid channels 122A can be spaced apart from one another between about 0.1 mm to about 1.0 mm. The two fluid channels of the second pair of fluid channels 122B can be spaced apart from one another. The two fluid channels of the second pair of fluid channels 122B can be spaced apart from one another between about 0.1 mm to about 1.0 mm.

In some embodiments, the first pair of fluid channels 122A and the second pair of fluid channels 122B can be positioned substantially on opposite sides of the optic portion 102. The first pair of fluid channels 122A can be positioned substantially diametrically opposed to the second pair of fluid channels 122B.

The first pair of fluid channels 122A and the second pair of fluid channels 122B can be defined or extend through part of the optic portion 102. The first pair of fluid channels 122A and the second pair of fluid channels 122B can be defined or extend through the posterior element 108.

A design with two fluid channels 122 rather than one channel helps maintain dimensional stability during assembly, which can be important when assembling flexible and thin components. Additionally, it was observed through experimentation that a design with two fluid channels 122 provided better optical quality than certain one-channel designs throughout the range of accommodation. The additional stiffness of the two fluid channel design results in less deflection due to pressure changes in the fluid channels.

Figure 1D:
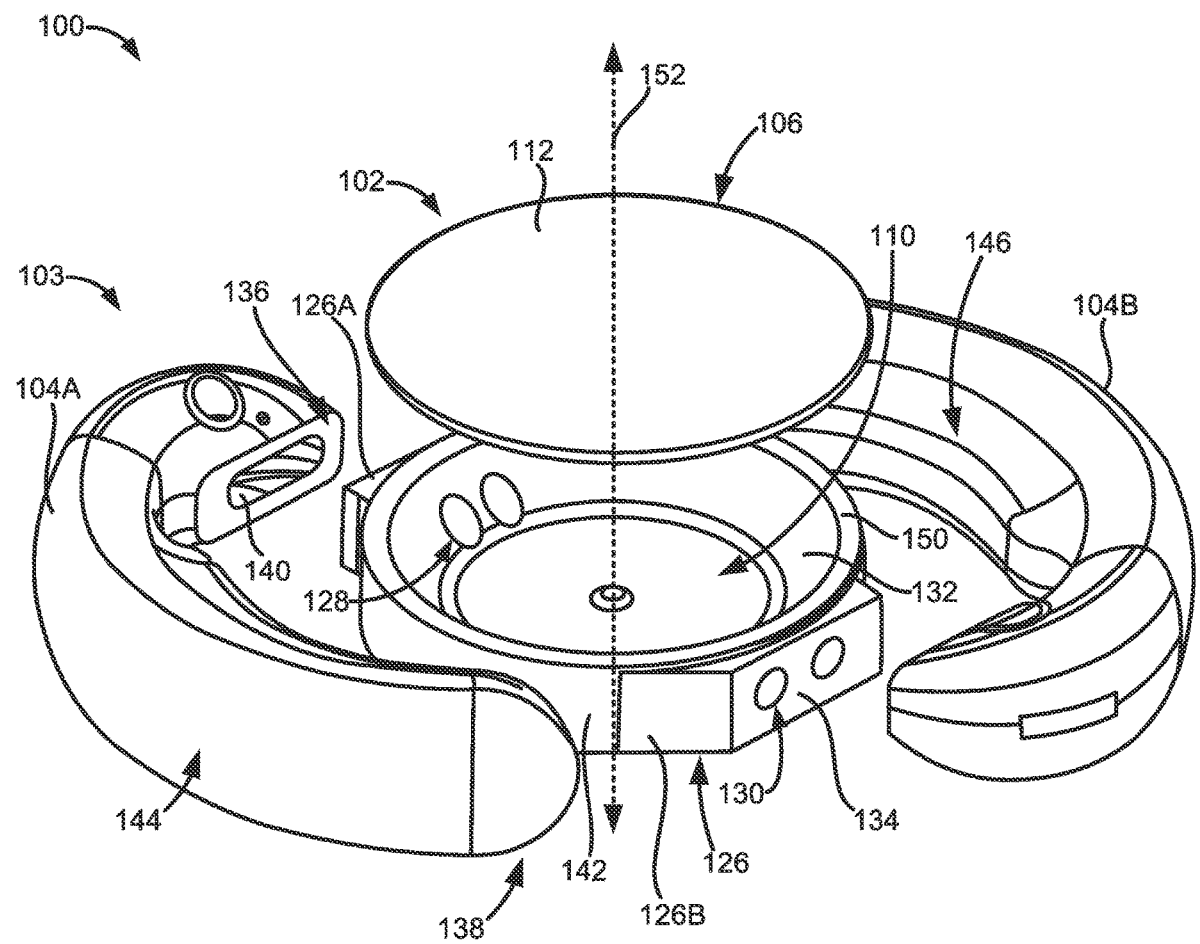
FIG. 1D illustrates an exploded view of an embodiment of the adjustable accommodating intraocular lens.

As shown in FIG. 1D, the optic portion 102 can comprise a first reinforced portion 126A and a second reinforced portion 126B substantially on opposing sides of the optic portion 102 or substantially diametrically opposed to one another. The first pair of fluid channels 122A can be defined or formed within the first reinforced portion 126A. The second pair of fluid channels 122B can be defined or formed within the second reinforced portion 126B.

The pair of fluid channels 122 (e.g., any of the first pair of fluid channels 122A or the second pair of fluid channels 122B) can have a pair of inner apertures 128 disposed at one end of the fluid channels 122 and another pair of outer apertures 130 disposed at the other end of the fluid channels 122. The pair of inner apertures 128 can be defined or formed on part of the posterior element 108. As shown in FIGS. 1B-1D, the inner apertures 128 can be defined or formed on part of a raised inner surface 132 of the posterior element 108. In some embodiments, the raised inner surface 132 can be a sloped or beveled surface.

The pair of outer apertures 130 can be defined or formed on part of a protruding outer surface 134 of the posterior element 108. The protruding outer surface 134 can be part of the reinforced portion 126. The protruding outer surface 134 can also be part of the haptic-optic interface 124.

For example, FIG. 1D shows a pair of inner apertures 128 disposed at one end of the first pair of fluid channels 122A and defined along the raised inner surface 132 of the posterior element 108. FIG. 1D also shows a pair of outer apertures 130 serving as ends of the second pair of fluid channels 122B and defined along the protruding outer surface 134 of the posterior element 108. The pair of outer apertures 130 of the first pair of fluid channels 122A and the pair of inner apertures 128 of the second pair of fluid channels 122B are obscured in FIG. 1D.

The two apertures of the pair of inner apertures 128 can be spaced apart from one another between about 0.1 mm to about 1.0 mm. The two apertures of the pair of outer apertures 130 can be spaced apart from one another between about 0.1 mm to about 1.0 mm. The pair of inner apertures 128 of the first pair of fluid channels 122A can be positioned diametrically opposed to or on opposite sides of the raised inner surface 132 from the pair of inner apertures 128 of the second pair of fluid channels 122B.

FIG. 1D also illustrates that each of the haptics 104 (e.g., any of the first haptic 104A or the second haptic 104B) can have an optic attachment end 136 and a closed free end 138. A haptic fluid port 140 can be defined at the optic attachment end 136 of the haptic 104. The haptic fluid port 140 can serve as a chamber opening of the haptic fluid chamber 120. Fluid within the haptic fluid chamber 120 can flow out of the haptic fluid chamber 120 through the haptic fluid port 140 and into the optic fluid chamber 110 via the pair of fluid channels 122 when the haptic 104 is coupled to the optic portion 102. Similarly, fluid within the optic fluid chamber 110 can flow out of the optic fluid chamber 110 through the pair of fluid channels 122 and into the haptic fluid chamber 120 through the haptic fluid port 140.

As shown in FIGS. 1A and 1D, a haptic 104 can couple to the optic portion 102 at a reinforced portion 126. For example, the first haptic 104A can couple or be attached to the optic portion 102 at the first reinforced portion 126A and the second haptic 104B can couple or be attached to the optic portion 102 at the second reinforced portion 126B.

More specifically, the haptic attachment end 136 can couple to the protruding outer surface 134 of the posterior element 108. The protruding outer surface 134 can also be referred to as a "landing" or "haptic attachment landing." The protruding outer surface 134 can extend out radially from an outer peripheral surface 142 of the optic portion 102. For example, the protruding outer surface 134 can extend out radially from an outer peripheral surface 142 of the posterior element 108 of the optic portion 102. The protruding outer surface 134 can extend out radially from the outer peripheral surface 142 between about 10 microns and 1.0 mm or between about 10 microns and 500 microns.

The haptic attachment end 136 can have a substantially flat surface to adhere or otherwise couple to a substantially flat surface of the protruding outer surface 134. When the haptic attachment end 136 is coupled to the protruding outer surface 134, the haptic fluid port 140 can surround the outer apertures 130 of the fluid channels 122. The haptics 104 can be coupled or adhered to the optic portion 102 via biocompatible adhesives 148. In some embodiments, the adhesives 148 can be the same adhesives used to couple or adhere the anterior element 106 to the posterior element 108. The adhesives 148 will be discussed in more detail in the following sections.

Each of the haptics 104 can also comprise a radially outer portion 144 configured to face and contact an inner surface of a patient's capsular bag when the adjustable AIOL 100 is implanted within the capsular bag. Each of the haptics 104 can also comprise a radially inner portion 146 configured to face the outer peripheral surface 142 of the optic portion 102. Engagement of the capsular bag with the radially outer portion 144 of the haptics 104 will be discussed in more detail in the following sections.

The optic portion 102 can have a base power or base spherical power. The base power of the optic portion 102 can be configured to change based on an internal fluid pressure within the fluid-filled optic fluid chamber 110. The base power of the optic portion 102 can be configured to increase or decrease as fluid enters or exits the fluid-filled optic fluid chamber 110.

The base power of the optic portion 102 can be configured to increase as fluid enters the fluid-filled optic fluid chamber 110 from the haptic fluid chamber(s) 120, as shown in FIG. 1B. The base power of the optic portion 102 can be configured to decrease as fluid exits or is drawn out of the fluid-filled optic fluid chamber 110 into the haptic fluid chamber(s) 120, as shown in FIG. 1C.

It should be noted that although FIG. 1B illustrates the fluid entering the optic fluid chamber 110 from the haptic fluid chambers 120 using the curved broken-line arrows, fluid enters the optic fluid chamber 110 via the fluid channels 122 (including through the inner apertures 128 and outer apertures 130) and haptic fluid ports 140. It should also be noted that although FIG. 1C illustrates the fluid exiting the optic fluid chamber 110 into the haptic fluid chambers 120 using the curved broken-line arrows, fluid exits the optic fluid chamber 110 via the fluid channels 122 (including through the inner apertures 128 and outer apertures 130) and haptic fluid ports 140.

The optic portion 102 can be made in part of a deformable or flexible material. In some embodiments, the optic portion 102 can be made in part of a deformable or flexible polymeric material. For example, the anterior element 106, the posterior element 108, or a combination thereof can be made in part of a deformable or flexible polymeric material. The one or more haptics 104 (e.g., the first haptic 104A, the second haptic 104B, or a combination thereof) can be made in part of the same deformable or flexible material as the optic portion 102. In other embodiments, the one or more haptics 104 can be made in part of different materials from the optic portion 102.

In some embodiments, the optic portion 102 can comprise or be made in part of a lens body material. The lens body material can be made in part of a cross-linked copolymer comprising a copolymer blend. The copolymer blend can comprise an alkyl acrylate or methacrylate, a fluoro-alkyl (meth)acrylate, and a phenyl-alkyl acrylate. It is contemplated by this disclosure and it should be understood by one of ordinary skill in the art that these types of acrylic cross-linked copolymers can be generally copolymers of a plurality of acrylates, methacrylates, or a combination thereof and the term "acrylate" as used herein can be understood to mean acrylates, methacrylates, or a combination thereof interchangeably unless otherwise specified. The cross-linked copolymer used to make the lens body material can comprise an alkyl acrylate in the amount of about 3% to 20% (wt %), a fluoro-alkyl acrylate in the amount of about 10% to 35% (wt %), and a phenyl-alkyl acrylate in the amount of about 50% to 80% (wt %). In some embodiments, the cross-linked copolymer can comprise or be made in part of an n-butyl acrylate as the alkyl acrylate, trifluoroethyl methacrylate as the fluoro-alkyl acrylate, and phenylethyl acrylate as the phenyl-alkyl acrylate. More specifically, the cross-linked copolymer used to make the lens body material can comprise n-butyl acrylate in the amount of about 3% to 20% (wt %) (e.g., between about 12% to 16%), trifluoroethyl methacrylate in the amount of about 10% to 35% (wt %) (e.g., between about 17% to 21%), and phenylethyl acrylate in the amount of about 50% to 80% (wt %) (e.g., between about 64% to 67%).

The final composition of the cross-linked copolymer used to make the lens body material can also comprise a cross-linker or cross-linking agent such as ethylene glycol dimethacrylate (EGDMA). For example, the final composition of the cross-linked copolymer used to make the lens body material can also comprise a cross-linker or cross-linking agent (e.g., EGDMA) in the amount of about 1.0%. The final composition of the cross-linked copolymer used to make the lens body material can also comprise an initiator or initiating agent (e.g., Perkadox 16) and a UV absorber.

The haptic(s) 104 can comprise or be made in part of a haptic material. The haptic material can comprise or be made in part of a cross-linked copolymer comprising a copolymer blend. The copolymer blend can comprise an alkyl acrylate, a fluoro-alkyl acrylate, and a phenyl-alkyl acrylate. For example, the cross-linked copolymer used to make the haptic material can comprise an alkyl acrylate in the amount of about 10% to 25% (wt %), a fluoro-alkyl acrylate in the amount of about 10% to 35% (wt %), and a phenyl-alkyl acrylate in the amount of about 50% to 80% (wt %). In some embodiments, the cross-linked copolymer used to make the haptic material can comprise n-butyl acrylate in the amount of about 10% to 25% (wt %) (e.g., between about 19% to about 23%), trifluoroethyl methacrylate in the amount of about 10% to 35% (wt %) (e.g., between about 14% to about 18%), and phenylethyl acrylate in the amount of about 50% to 80% (wt %) (e.g., between about 58% to about 62%). The final composition of the cross-linked copolymer used to make the haptic material can also comprise a cross-linker or cross-linking agent, such as EGDMA, in the amount of about 1.0%. The final composition of the cross-linked copolymer used to make the haptic material can also comprise a number of photoinitiators or photoinitiating agents (e.g., camphorquinone, 1-phenyl-1,2-propanedione, and 2-ethylhexyl-4-(dimenthylamino)benzoate).

In some embodiments, the refractive index of the lens body material can be between about 1.48 and about 1.53. In certain embodiments, the refractive index of the lens body material can be between about 1.50 and about 1.53 (e.g., about 1.5178).

The optic portion 102 can be configured to deform, flex, or otherwise change shape (see FIGS. 1B and 1C) in response to fluid entering or exiting the optic fluid chamber 110. The optic portion 102 can be configured to deform, flex, or otherwise change shape as a result of the material composition (e.g., the polymeric composition) of the optic portion 102 discussed heretofore. The haptic(s) 104 can also be configured to deform or otherwise change shape in response to interactions or engagement with the capsular bag of a patient when the adjustable AIOL 100 is implanted within an eye of the patient. The haptic(s) 104 can be configured to deform or otherwise change shape as a result of the material composition of the haptics 104.

In some embodiments, the anterior element 106 can be configured to deform, flex, or otherwise change shape (e.g., change its curvature) in response to fluid entering or exiting the optic fluid chamber 110. In other embodiments, the posterior element 108 can be configured to deform, flex, or otherwise change shape (e.g., change its curvature) in response to fluid entering or exiting the optic fluid chamber 110. In further embodiments, both the anterior element 106 and the posterior element 108 can be configured to deform, flex, or otherwise change their shapes in response to fluid entering or exiting the optic fluid chamber 110.

In some embodiments, the fluid within the optic fluid chamber 110, the haptic fluid chamber(s) 120, or a combination thereof can be an oil. More specifically, in certain embodiments, the fluid within the optic fluid chamber 110, the haptic fluid chamber(s) 120, or a combination thereof can be a silicone oil or fluid. The fluid can flow between the optic fluid chamber 110 and the haptic fluid chamber(s) 120 in response to a deformation, flexing, or shape change undertaken by the haptic(s) 104, component(s) of the optic portion 102 (e.g., the anterior element 106, the posterior element 108, or a combination thereof), or a combination thereof.

The fluid within the optic fluid chamber 110, the haptic fluid chamber(s) 120, or a combination thereof can be a silicone oil or fluid comprising or made in part of a diphenyl siloxane. In other embodiments, the silicone oil or fluid can comprise or be made in part of a ratio of two dimethyl siloxane units to one diphenyl siloxane unit. More specifically, in some embodiments, the silicone oil or fluid can be a diphenyltetramethyl cyclotrisiloxane. In additional embodiments, the silicone oil or fluid can comprise or be made in part of a diphenyl siloxane and dimethyl siloxane copolymer.

The fluid (e.g., the silicone oil) can be index matched with the lens body material used to make the optic portion 102. When the fluid is index matched with the lens body material, the entire optic portion 102 containing the fluid acts as a single lens. For example, the fluid can be selected so that it has a refractive index of between about 1.48 and 1.53 (or between about 1.50 and 1.53). In some embodiments, the fluid (e.g., the silicone oil) can have a polydispersity index of between about 1.2 and 1.3. In other embodiments, the fluid (e.g., the silicone oil) can have a polydispersity index of between about 1.3 and 1.5. In other embodiments, the fluid (e.g., the silicone oil) can have a polydispersity index of between about 1.1 and 1.2. Other example fluids are described in U.S. Patent Publication No. 2018/0153682, which is herein incorporated by reference in its entirety.

The base power of the optic portion 102 can be configured to change in response to the shape change undertaken by the shape-changing components of the optic portion 102 (e.g., the anterior element 106, the posterior element 108, or a combination thereof). The optic portion 102 can be configured to change shape in response to a physiologic muscle movement (e.g., ciliary muscle movement) undertaken by a patient when the adjustable AIOL 100 is implanted within a capsular bag of the eye of the patient and the adjustable AIOL 100 deforms or changes shape in response to ciliary muscle related capsular bag reshaping.

The adjustable AIOL 100 can be implanted or introduced into a patient's capsular bag after a native lens has been removed from the capsular bag. The patient's capsular bag is connected to zonule fibers which are connected to the patient's ciliary muscles. The capsular bag is elastic and ciliary muscle movements can reshape the capsular bag via the zonule fibers. For example, when the ciliary muscles relax, the zonules are stretched. This stretching pulls the capsular bag in the generally radially outward direction due to radially outward forces. This pulling of the capsular bag causes the capsular bag to elongate, creating room within the capsular bag. When the patient's native lens is present in the capsular bag, the native lens normally becomes flatter (in the anterior-to-posterior direction), which reduces the power of the lens, allowing for distance vision. In this configuration, the patient's native lens is said to be in a disaccommodated state or undergoing disaccommodation.

When the ciliary muscles contract, however, as occurs when the eye is attempting to focus on near objects, the radially inner portion of the muscles move radially inward, causing the zonules to slacken. The slack in the zonules allows the elastic capsular bag to contract and exert radially inward forces on a lens within the capsular bag. When the patient's native lens is present in the capsular bag, the native lens normally becomes more curved (e.g., the anterior part of the lens becomes more curved), which gives the lens more power, allowing the eye to focus on near objects. In this configuration, the patient's native lens is said to be in an accommodated state or undergoing accommodation.

Therefore, any AIOLs implanted within the capsular bag should also possess mechanisms which allow for the base power of the AIOL to increase when the ciliary muscles contract and allow for the base power of the AIOL to decrease when the ciliary muscles relax.

In the present case, when the adjustable AIOL 100 is implanted or otherwise introduced into a patient's native capsular bag, the radially outer portions 144 of the haptics 104 of the adjustable AIOL 100 can directly engage with or be in physical contact with the portion of the capsular bag that is connected to the zonules or zonule fibers. Therefore, the radially outer portions 144 of the haptics 104 can be configured to respond to capsular bag reshaping forces that are applied radially when the zonules relax and stretch as a result of ciliary muscle movements.

When the ciliary muscles contract, the peripheral region of the elastic capsular bag reshapes and applies radially inward forces on the radially outer portions 144 of the haptics 104 (for example, the elastic capsular bag applies radially inward forces on the radially outer portion 144 of the first haptic 104A and on the radially outer portion 144 of the second haptic 104B). The radially outer portions 144 of the haptics 104 then deform or otherwise changes shape and this deformation or shape change causes the volume of the haptic fluid chambers 120 to decrease. When the volume of the haptic fluid chambers 120 decreases, the fluid within the haptic fluid chambers 120 is moved or pushed into the optic fluid chamber 110 within the optic portion 102. As discussed previously, fluid moves from the haptic fluid chamber 120 into the optic fluid chamber 110 through fluid channels 122 (e.g., a pair of fluid channels 122) formed within the optic portion 102.

The optic portion 102 (any of the anterior element 106, the posterior element 108, or a combination thereof) can change shape (increase its curvature) in response to the fluid entering the optic fluid chamber 110 from the haptic fluid chambers 120. This increases the base power or base spherical power of the adjustable AIOL 100 and allows a patient with the adjustable AIOL 100 implanted within the eye of the patient to focus on near objects. The adjustable AIOL 100 can also be considered to be in an accommodated state or have undergone accommodation.

When the ciliary muscles relax, the peripheral region of the elastic capsular bag is stretched radially outward and the capsular bag elongates and more room is created within the capsular bag. The radially outer portions 144 of the haptics 104 can be configured to respond to this capsular bag reshaping by returning to its non-deformed or non-stressed configuration. This causes the volume of the haptic fluid chambers 120 to increase or return to its non-deformed volume. This increase in the volume of the haptic fluid chambers 120 causes the fluid within the optic fluid chamber 110 to be drawn out or otherwise flow out of the optic fluid chamber 110 and back into the haptic fluid chambers 120. As discussed previously, fluid moves out of the optic fluid chamber 110 into the haptic fluid chamber 120 through the same fluid channels 122 (e.g., a pair of fluid channels 122) formed within the optic portion 102.

As previously discussed, the optic portion 102 (any of the anterior element 106, the posterior element 108, or a combination thereof) can change shape (decrease its curvature or become flatter) in response to the fluid exiting the optic fluid chamber 110 and into the haptic fluid chambers 120. This decreases the base power or base spherical power of the adjustable AIOL 100 and allows a patient with the adjustable AIOL 100 implanted within the eye of the patient to focus on distant objects or provide for distance vision. The adjustable AIOL 100 can also be considered to be in a disaccommodated state or have undergone disaccommodation.

As shown in FIGS. 1B and 1C, the radially inner portion 146 of the haptics 104 can be designed to be thicker or bulkier (relative to the radially outer portion 144) to provide the haptics 104 with stiffness or resiliency in the anterior-to-posterior direction. This way, when capsular bag forces are applied to the haptics 104 in the anterior-to-posterior direction, less deformation occurs and less fluid movement occurs between the haptic fluid chambers 120 and the optic fluid chamber 110 than when forces are applied in the radial direction. Since less fluid movement occurs, less changes in the base power of the adjustable AIOL 100 occur when forces are applied to the adjustable AIOL 100 in the anterior-to-posterior direction. Thus, the design and material properties of the haptics 104 and the optic portion 102 can allow the adjustable AIOL 100 to maintain a high degree of sensitivity to radial forces applied to the haptics 104 by capsular bag reshaping caused by ciliary muscle movements.

In some embodiments, the anterior element 106 can be configured such that the anterior optical surface 112 changes shape from a spherical surface configuration to an aspherical surface configuration in response to fluid entering the optic fluid chamber 110. An aspherical surface configuration can correct for high order aberrations such as spherical aberration. The fluid can enter the optic fluid chamber 110 from one or more haptic fluid chambers 120 coupled to the optic portion 102 in response to ciliary muscle movement.

The anterior optical surface 112 can be stressed into the aspherical surface configuration as a center or central portion of the anterior element 106 flexes or bulges out further than an outer periphery of the anterior element 106 which is held down by adhesives 148 or an adhesive layer (see FIGS. 1B and 1C).

In other embodiments, the posterior element 108 can be configured such that the posterior optical surface 116 changes shape from a spherical surface configuration to an aspherical surface configuration in response to fluid entering the optic fluid chamber 110.

The posterior optical surface 116 can be stressed into the aspherical surface configuration as a center or central portion of the posterior element 108 flexes or bulges out further than an outer periphery of the anterior element 106 which is held down by adhesives 148 or the adhesive layer.

The anterior element 106 can be attached or otherwise adhered to the posterior element 108 via adhesives 148 or an adhesive layer. The adhesive layer can be substantially annular-shaped. The adhesives 148 or adhesive layer can be positioned at a peripheral edge 150 (see FIG. 1D) of the optic portion 102 in between the anterior element 106 and the posterior element 108. For example, the adhesives 148 can be positioned on top of the raised inner surface 132 of the posterior element 108.

The adhesives 148 or adhesive layer can comprise or be made in part of a biocompatible adhesive. The adhesives 148 or adhesive layer can comprise or be made in part of a biocompatible polymeric adhesive.

The adhesives 148 or adhesive layer can comprise or be made in part of a cross-linkable polymer precursor formulation. The cross-linkable polymer precursor formulation can comprise or be made in part of a copolymer blend, a hydroxyl-functional acrylic monomer, and a photoinitiator.

The copolymer blend can comprise an alkyl acrylate (e.g., n-butyl acrylate in the amount of about 41% to about 45% (wt %)), a fluoro-alkyl acrylate (e.g., trifluoroethyl methacrylate in the amount of about 20% to about 24% (wt %)), and a phenyl-alkyl acrylate (phenylethyl acrylate in the amount of about 28% to about 32% (wt %)). The hydroxyl-functional acrylic monomer can be 2-hydroxyethyl acrylate (HEA). The photoinitiator can be used to facilitate curing of the adhesive. For example, the photoinitiator can be Darocur 4265 (a 50/50 blend of diphenyl(2,4,6-trimethylbenzoyl) phosphine oxide and 2-hydroxy2-methylpropiophenone).

The first step in making the adhesive is preparation of a hydroxyl-functional polymer precursor by photopolymerizing the cross-linkable polymer precursor formulation, thereby yielding a cured composition. The second step is chemical conversion of the precursor polymer pendant hydroxyl moieties, or hydroxyl pendant groups, into pendant methacrylate functional groups by reacting with a methacrylic anhydride or methacryloyl chloride, thus forming a methacrylate-functional or methacrylic-functional cross-linkable polymer comprising the alkyl acrylate or methacrylate (e.g., n-butyl acrylate), the fluoro-alkyl (meth)acrylate (e.g., trifluoroethyl methacrylate), the phenyl-alkyl acrylate (phenylethyl acrylate), and 2-(2-methyl-acryloyloxy)ethyl acrylate.

The methacrylic-functional cross-linkable polymer can be blended with a reactive acrylic monomer diluent such as 1-adamantyl methacrylate (ADMA) and the same photoinitiator (e.g., Darocur 4265). For example, the final composition of the adhesives 148 can comprise the cross-linkable polymer precursor formulation in the amount of about 50% to about 85% (wt %) (e.g., about 61% to about 65%), the reactive acrylic monomer diluent in the amount of about 10% to about 40% (wt %) (32% to about 36%), and the photoinitiator (e.g., Darocur 4265) in the amount of about 2% to about 3% (wt %).

The adhesives 148 or adhesive layer can bond, adhere, or otherwise join the anterior element 106 to the posterior element 108. As will be discussed in more detail in the following sections, the thickness of the adhesive layer can be adjusted post-implantation to adjust a base power of the adjustable AIOL 100.

In some embodiments, the same adhesives 148 used to bond the anterior element 106 to the posterior element 108 can also be used to bond or affix the peripheral portion 103 (e.g., the one or more haptics 104) to the optic portion 102.

In certain embodiments, the anterior optical surface 112 of the anterior element 106 can be manufactured to have an aspherical optical surface prior to the adjustable AIOL 100 being implanted within the eye of the patient. In these embodiments, the anterior optical surface 112 can be aspheric regardless of any fluid pressure changes within the optic fluid chamber 110. In these embodiments, the anterior optical surface 112 can also maintain its asphericity across all base power changes.

In other embodiments, the posterior optical surface 116 of the posterior element 108 can be manufactured to have an aspherical optical surface prior to the adjustable AIOL 100 being implanted within the eye of the patient. In these embodiments, the posterior optical surface 116 can be aspheric regardless of any fluid pressure changes within the optic fluid chamber 110. In these embodiments, the posterior optical surface 116 can maintain its asphericity across all base power changes.

In some embodiments, the anterior element 106 can have a thickness at its center or central portion that is greater than a thickness at its periphery. In certain embodiments, the posterior element 108 can also have a thickness at its center or central portion that is greater than a thickness at its periphery.

As shown in FIGS. 1B-1D, the optic portion 102 can have an optical axis 152. The optical axis 152 can extend in an anterior-to-posterior direction through a center or center point of the optic portion 102. The optical axis 152 can extend through the centers or center points of both the anterior element 106 and the posterior element 106.

The thickness of the anterior element 106 can be greater at the optical axis 152 or near the optical axis 152 than at the periphery of the anterior element 106. In some embodiments, the thickness of the anterior element 106 can increase gradually from the periphery of the anterior element 106 toward the optical axis 152.

In certain embodiments, the thickness of the anterior element 106 at the optical axis 152 or near the optical axis 152 can be between about 0.45 mm and about 0.55 mm. In these and other embodiments, the thickness of the anterior element 106 near the periphery can be between about 0.20 mm and about 0.40 mm. This difference in thickness can contribute to the anterior optical surface 112 changing shape from a spherical surface configuration to an aspherical surface configuration as fluid enters the fluid-filled optic fluid chamber 110 from the haptic fluid chamber(s) 120.

Moreover, the anterior inner surface 114 of the anterior element 106 can have less curvature or be flatter than the anterior optical surface 112. This difference in surface curvature between the anterior inner surface 114 and the anterior optical surface 112 can also contribute to the anterior optical surface 112 changing shape from the spherical surface configuration to the aspherical surface configuration as fluid enters the fluid-filled optic fluid chamber 110 from the haptic fluid chamber(s) 120.

In other embodiments, the thickness of the posterior element 108 can be greater at the optical axis 152 or near the optical axis 152 than portions of the posterior element 108 radially outward from the optical axis 152 but prior to reaching the raised inner surface 132. The thickness of the posterior element 108 can gradually decrease from the optical axis 152 to portions radially outward from the optical axis 152 (but prior to reaching the raised inner surface 132). The thickness of the posterior element 108 can increase again from the beginning of the raised inner surface 132 to the peripheral edge 150.

In certain embodiments, the thickness of the posterior element 108 at the optical axis 152 or near the optical axis 152 can be between about 0.45 mm and about 0.55 mm. In these and other embodiments, the thickness of the posterior element 108 radially outward from the optical axis 152 (but prior to reaching the raised inner surface 132) can be between about 0.20 mm and about 0.40 mm. The thickness of the posterior element 108 near the peripheral edge 150 can be between about 1.00 mm and 1.15 mm. This difference in thickness can contribute to the posterior optical surface 116 changing shape from the spherical surface configuration to the aspherical surface configuration as fluid enters the fluid-filled optic fluid chamber 110 from the haptic fluid chamber(s) 120.

Moreover, the posterior inner surface 118 of the posterior element 108 can have less curvature or be flatter than the posterior optical surface 116. This difference in surface curvature between the posterior inner surface 118 and the posterior optical surface 116 can also contribute to the posterior optical surface 116 changing shape from the spherical surface configuration to the aspherical surface configuration as fluid enters the fluid-filled optic fluid chamber 110 from the haptic fluid chamber(s) 120.

Figure 2A:
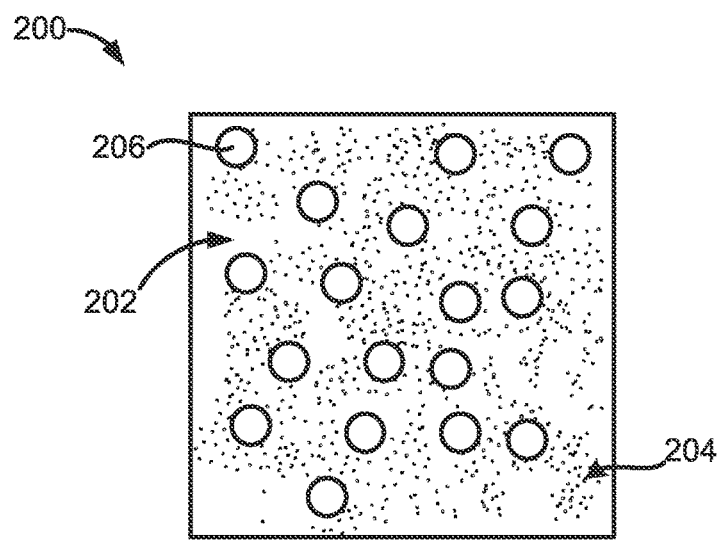
FIG. 2A illustrates a composite material used to make at least part of the adjustable accommodating intraocular lens.

FIG. 2A is a graphic representation of a composite material 200 comprising a composite base material 202, an energy absorbing constituent 204, and a plurality of expandable components 206. In some embodiments, the optic portion 102 of the adjustable AIOL 100 can be made in part of the composite material 200. In other embodiments, the peripheral portion 103 of the adjustable AIOL 100 can be made in part of the composite material 200. In further embodiments, both the optic portion 102 and the peripheral portion 103 of the adjustable AIOL 100 can be made in part of the composite material 200.

The composite base material 202 can comprise a methacrylate-functional or methacrylic-functional cross-linkable polymer and reactive acrylic monomer diluents including lauryl methacrylate (n-dodecyl methacrylate or SR313) and ADMA. By controlling the amount of lauryl methacrylate (SR313) to ADMA, the overall corresponding hardness (i.e., more ADMA) or softness (i.e., more SR313) of the cured composite material 200 can be controlled. The methacrylate-functional or methacrylic-functional cross-linkable polymer can be made using the cross-linkable polymer precursor formulation. The cross-linkable polymer precursor formulation can be the same cross-linkable polymer precursor formulation used as part of the formulation for the adhesives 148.

As previously discussed, the optic portion 102 can comprise or be made in part of the lens body material. Also, as previously discussed, the peripheral portion 103 (e.g., the one or more haptics 104) can comprise or be made in part of the haptic material. The cross-linkable polymer precursor formulation can comprise the same copolymer blend used to make the lens body material, the haptic material, or the adhesives.

The copolymer blend can comprise an alkyl acrylate or methacrylate (e.g., n-butyl acrylate), a fluoro-alkyl (meth)acrylate (e.g., trifluoroethyl methacrylate), and a phenyl-alkyl acrylate (e.g., phenylethyl acrylate). For example, the copolymer blend can comprise n-butyl acrylate in the amount of about 41% to about 45% (wt %), trifluoroethyl methacrylate in the amount of about 20% to about 24% (wt %), and phenylethyl acrylate in the amount of about 28% to about 32% (wt %). As previously discussed, the cross-linkable polymer precursor formulation can comprise or be made in part of the copolymer blend, a hydroxyl-functional acrylic monomer (e.g., HEA), and a photoinitiator (e.g., Darocur 4265 or a 50/50 blend of diphenyl(2,4,6-trimethylbenzoyl)-phosphine oxide and 2-hydroxy2-methylpropiophenone).

The composite base material 202 can comprise the methacrylate-functional or methacrylic-functional cross-linkable polymer (as discussed above) in the amount of about 50% to about 65% (e.g., about 55% to about 60%) (wt %), the reactive acrylic monomer diluent lauryl methacrylate (SR313) in the amount of about 32% to about 38% (e.g., about 32.70%) (wt %), the reactive acrylic monomer diluent adamantly methacrylate (ADMA) in the amount of about 5% to about 9% (e.g., about 7.30%) (wt %).

The composite material 200 can be made in several operations. The first operation can comprise preparing an uncolored composite base material 202. The second operation can comprise mixing the composite base material 202 with an energy absorbing constituent 204, expandable components 206, and initiators such as one or more photoinitiators, thermal initiators, or a combination thereof. The third operation can comprise placing the uncured composite material 200 into a desired location within the optic portion 102, the haptic(s) 104, or a combination thereof, and curing the composite material 200 in place to form the adhered composite material 200.

For example, the uncolored composite base material 202 can be mixed with an energy absorbing constituent 204 such as a dye (e.g., Disperse Red 1 dye) or pigment (graphitized carbon black). The energy absorbing constituent 204 will be discussed in more detail below.

In some embodiments, the expandable components 206 can make up about 5.0% to about 15.0% by weight of a final formulation of the composite material 200. More specifically, the expandable components 206 can make up about 8.0% to about 12.0% (e.g., about 10.0%) by weight of a final formulation (see Table 1) of the composite material 200. In these and other embodiments, the energy absorbing constituent 204 can make up about 0.044% to about 0.44% (or about 0.55%) by weight of the final formulation of the composite material 200.

The photoinitiator can be Omnirad 2022 (bis(2,4,6-trimethylbenzoyl)phenyl-phosphineoxide/2-hydroxy-2-methyl-1-phenyl-propan-1-one). The photoinitiator can make up about 1.30% by weight of a final formulation of the composite material 200 (see, e.g., Table 1). In addition, the composite material 200 can also comprise a thermal initiator. The thermal initiator can make up about 1.00% by weight of a final formulation of the composite material 200 (see, e.g., Table 1). In some embodiments, the thermal initiator can be a dialkyl peroxide such as Luperox® peroxide. In other embodiments, the thermal initiator can be Perkadox.

TABLE 1

| FORMULATION OF COMPOSITE MATERIAL (WT %) | |
|---|---|
| Cross-linkable polymer (in two steps from precursor formulation, as described above) | 1.47% 2-hydroxyethyl acrylate (HEA)<br>1.96% Darocur 4265 (photoinitiator)<br>43.50% n-butylacrylate (nBA)<br>30.21% 2-phenylethylacrylate (PEA)<br>22.87% 2,2,2-trifluoroethylmethacrylate (TFEMA) |
| Composite base material | 60.00% cross-linkable polymer<br>32.70% lauryl methacrylate (SR313)<br>7.30% 1-adamantyl methacrylate (ADMA) |
| Composite base material with red energy absorbing colorant | 99.50% composite base material<br>0.50% Disperse Red 1 dye |
| Composite base material with black energy absorbing colorant | 99.95% composite base material<br>0.05% graphitized mesoporous carbon black |
| Final formulation of composite material | 87.70% composite base material with red or black energy absorbing colorant<br>10.00% expandable microspheres<br>1.00% Luperox peroxide (thermal initiator)<br>1.30% Omnirad 2022 |

Figure 2B:
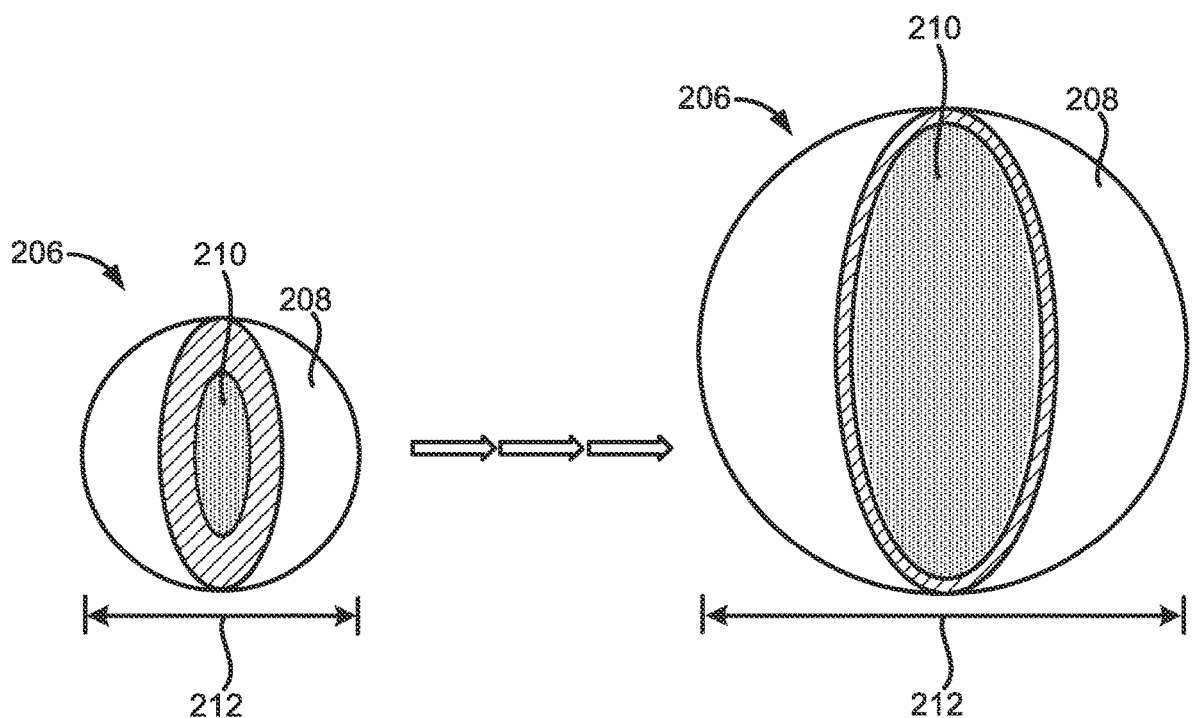
FIG. 2B illustrates one embodiment of an expandable component of the composite material.

FIG. 2B illustrates that the expandable components 206 can be expandable microspheres comprising an expandable thermoplastic shell 208 and a blowing agent 210 contained within the expandable thermoplastic shell 208. The microspheres can be configured to expand such that a diameter 212 of at least one of the microspheres can increase about 2× the original diameter. In other embodiments, the microspheres can be configured to expand such that the diameter 212 of at least one of the microspheres can increase about 4× or four times the original diameter. In further embodiments, the microspheres can be configured to expand such that the diameter 212 of at least one of the microspheres can increase between about 2× and about 4× (or about 3.5×) the original diameter. For example, the microspheres can have a diameter 212 of about 12 µm at the outset. In response to an external energy applied or directed at the composite material 200 or in response to energy transferred or transmitted to the microspheres, the diameter 212 of the microspheres can increase to about 40 µm.

The volume of at least one of the microspheres can be configured to expand between about ten times (10×) to about 50 times (50×) in response to the external energy applied or directed at the composite material 20 or in response to energy transferred or transmitted to the microspheres.

In some embodiments, the blowing agent 210 can be an expandable fluid, such as an expandable gas. More specifically, the blowing agent 210 can be a branched-chain hydrocarbon. For example, the blowing agent 210 can be isopentane. In other embodiments, the blowing agent 210 can be or comprise cyclopentane, pentane, or a mixture of cyclopentane, pentane, and isopentane.

FIG. 2B illustrates that each of the expandable components 206 can comprise a thermoplastic shell 208. FIG. 2B also illustrates that a thickness of the thermoplastic shell 208 can change as the expandable component 206 increases in size. More specifically, the thickness of the thermoplastic shell 208 can decrease as the expandable component 206 increases in size. For example, when the expandable components 206 are expandable microspheres, the thickness of the thermoplastic shell 208 (i.e., its thickness in a radial direction) can decrease as the diameter 212 of the expandable microsphere increases.

For example, as previously discussed, at least one of the expandable microspheres can have a diameter 212 of about 12 µm at the outset. In this embodiment, the thermoplastic shell 208 of the expandable microsphere can have a shell thickness of about 2.0 µm. In response to an external energy applied or directed at the composite material 200 or in response to energy transferred or transmitted to the microsphere, the diameter 212 of the microsphere can increase to about 40 µm (and the volume expand between about 10× and 50×) and the shell thickness of the microsphere can decrease to about 0.1 µm.

Although FIGS. 2A and 2B illustrate the expandable components 206 as spheres or microspheres, it is contemplated by this disclosure that the expandable components 206 can be substantially shaped as ovoids, ellipsoids, cuboids or other polyhedrons, or a combination thereof.

In some embodiments, the thermoplastic shell 208 can be made in part of nitriles or acrylonitrile copolymers. For example, the thermoplastic shell 208 can be made in part of acrylonitrile, styrene, butadiene, methyl acrylate, or a combination thereof.

As previously discussed, the expandable components 206 can make up between about 8.0% to about 12% by weight of a final formulation of the composite material 200. The expandable components 206 can make up about 10% by weight of a final formulation of the composite material 200.

The expandable components 206 can be dispersed or otherwise distributed within the composite base material 202 making up the bulk of the composite material 200. The composite base material 202 can serve as a matrix for holding or carrying the expandable components 206. The composite material 200 can expand in response to an expansion of the expandable components 206 (e.g., the thermoplastic microspheres). For example, a volume of the composite material 200 can increase in response to the expansion of the expandable components 206.

The composite material 200 also comprises an energy absorbing constituent 204. In some embodiments, the energy absorbing constituent 204 can be an energy absorbing colorant.

In certain embodiments, the energy absorbing colorant can be an energy absorbing dye. For example, the energy absorbing dye can be an azo dye. In some embodiments, the azo dye can be a red azo dye such as Disperse Red 1 dye. In other embodiments, the azo dye can be an orange azo dye such as Disperse Orange dye (e.g., Disperse Orange 1), a yellow azo dye such as Disperse Yellow dye (e.g., Disperse Yellow 1), a blue azo dye such as Disperse Blue dye (e.g., Disperse Blue 1), or a combination thereof.

In additional embodiments, the energy absorbing colorant can be or comprise a pigment. For example, the energy absorbing colorant can be or comprise graphitized carbon black as the pigment.

Similar to the expandable components 206, the energy absorbing constituent 204 can be dispersed or otherwise distributed within the composite base material 202 making up the bulk of the composite material 200. The composite base material 202 can serve as a matrix for holding or carrying the expandable components 206 and the energy absorbing constituent 204.

As previously discussed, the energy absorbing constituent 204 can make up between about 0.025% to about 1.0% (or, more specifically, about 0.045% to about 0.45%) by weight of a final formulation of the composite material 200. For example, when the energy absorbing constituent 204 is a dye (e.g., an azo dye such as Disperse Red 1), the energy absorbing constituent 204 can make up about between about 0.45% to about 1.0% by weight of a final formulation of the composite material 200. When the energy absorbing constituent 204 is graphitized carbon black or other types of pigments, the energy absorbing constituent 204 can make up about 0.025% to about 0.045% by weight of a final formulation of the composite material 200.

The energy absorbing constituent 204 (e.g., azo dye, graphitized carbon black, or a combination thereof) can absorb or capture an external energy applied or directed at the composite material 200. The energy absorbing constituent 204 can absorb or capture the external energy and then transform or transfer the energy into thermal energy or heat to the expandable components 206.

The thermoplastic shell 208 can soften and begin to flow as thermal energy is transferred or transmitted to the expandable components 206. The thermoplastic shell 208 of the expandable components 206 can then begin to thin or reduce in thickness in response to the thermal energy transferred or transmitted to the expandable components 206. As the thermoplastic shell 208 begins to soften and reduce in thickness, the blowing agent 210 within the expandable components 206 can expand. The blowing agent 210 can also expand in response to the thermal energy or heat transferred or transmitted to the expandable components 206. Expansion of the blowing agents 210 can cause the expandable components 206 (e.g., the thermoplastic microspheres) to expand or increase in volume. This ultimately causes the composite material 200 to expand or increase in volume.

The composite material 200 can expand or increase in size in an isotropic manner such that the composite material 200 expands in all directions. Such isotropic expansion can be harnessed to produce expansion or material displacement in specific directions by placing or positioning the composite material 200 at specific locations along the haptic(s) 104 or optic portion 102 of the adjustable AIOL 100.

As will be discussed in more detail in the following sections, in some embodiments, the external energy can be light energy and the energy absorbing constituent 204 can absorb or capture the light energy directed at the composite material 200 and transform or transfer the light energy into thermal energy or heat to the expandable components 206. The blowing agent 210 within the expandable components 206 can expand or become energized in response to the thermal energy or heat. The expandable components 206 and, ultimately, the composite material 200 can expand or increase in volume in response to this light energy directed at the composite material 200.

The shape change (e.g., increase in volume) undertaken by the expandable components 206 can be a persistent change or a substantially permanent change. A persistent change or substantially permanent change can mean that the expandable components 206 do not substantially revert back to its original shape or size after the shape change (e.g., after an increase in volume) has occurred. As a result, any change in the size or volume of the composite material 200 caused by a change in the size or volume of the expandable components 206 is also persistent or substantially permanent. As will be discussed in more detail in the following sections, this means that any structural changes made to the adjustable AIOL 100 as a result of external energy or stimulus applied or otherwise directed at the composite material 200 embedded or integrated within the adjustable AIOL 100 can persist or remain substantially permanent.

The thermoplastic shells 208 of the expandable components 206 can harden, once again, when the external energy is no longer directed or applied to the composite material 200. The thermoplastic shells 208 of the expandable components 206 can harden, once again, when the temperature within a vicinity of the expandable components 206 falls below a certain threshold. For example, the thermoplastic shells 208 of the expandable microspheres can harden when light energy is no longer directed at the composite material 200. After the thermoplastic shells 208 harden, the expandable components 206 are locked into their new size and expanded configuration.

When the energy absorbing constituent 204 is an energy absorbing colorant, such as a dye or graphitized carbon, the color of at least part of the composite material 200 can take on the color of the energy absorbing colorant. For example, when the energy absorbing constituent 204 is an azo dye such as Disperse Red 1 having a red color, at least a portion of the composite material 200 comprising the energy absorbing constituent 204 can be colored red. Moreover, when the energy absorbing constituent 204 is graphitized carbon having a black color, at least a portion of the composite material 200 comprising the energy absorbing constituent 204 can be colored black. Although two colors (e.g., red and black) are mentioned in this disclosure, it is contemplated by this disclosure and it should be understood by one of ordinary skill in the art that energy absorbing colorant of other types of colors can also be used such as energy absorbing yellow, orange, or blue dyes or materials.

The color of the energy absorbing colorant can be visually perceptible to a clinician or another medical professional when the adjustable AIOL 100 is made in part of the composite material 100 comprising the energy absorbing colorant. The color of the energy absorbing colorant can be visually perceptible to a clinician or another medical professional when the adjustable AIOL 100 is implanted within an eye of a patient. For example, the composite material 200 can comprise Disperse Red 1 serving as the energy absorbing colorant. In this example, at least part of the adjustable AIOL 100 can appear red to the clinician or another medical professional when the adjustable AIOL 100 is implanted within the eye of a patient.

The color of the energy absorbing colorant can allow the clinician or another medical professional detect or determine the location or position of the composite material 200 within the adjustable AIOL 100. The color of the energy absorbing colorant can also allow the clinician or another medical professional to determine where to direct the external energy or stimulus to adjust the adjustable AIOL 100.

As will be discussed in more detail in the following sections, at least part of the adjustable AIOL 100 can be made of a composite material 200 comprising an energy absorbing constituent 204 of a first color (e.g., red) and another part of the adjustable AIOL 100 can be made of additional composite material 200 comprising an energy absorbing constituent 204 of a second color (e.g., black). By designing the adjustable AIOL 100 in this manner, a clinician or another medical professional can direct external energy or stimulus at different parts of the adjustable AIOL 100 using the different colors of the composite materials 200 as guides or markers for distinguishing between different locations of such target sites. Moreover, the different colored composite materials 200 can also serve as indicators or visual cues as to where to direct the external energy or stimulus to cause certain changes in one or more optical parameters (e.g., the base power, the cylindricity, or a combination thereof) of the adjustable AIOL 100.

One technical problem faced by the applicants is how to integrate an adjustable composite material into an optic portion and a peripheral portion (e.g., the haptics) of an AIOL such that the adjustable composite material would adhere to the lens material used to make the rest of the AIOL and remain substantially fixed at certain locations within the optic portion or peripheral portion. One solution discovered by the applicants and disclosed herein is the unique composition of the composite material which incorporates the same copolymer blend used to make the lens body material and the haptic material. Moreover, the composite material is made in part in the cross-linkable polymer precursor formulation used in the adhesive for adhering parts of the AIOL to one another. By designing the AIOL in this manner, the composite material is compatible with the rest of the material used to construct the optic portion and the peripheral portion and remains substantially fixed at its location without migrating or shifting.

Another technical problem faced by the applicants is how to ensure that any adjustments made to the AIOL persist long after the adjustment procedure. One solution discovered by the applicants and disclosed herein is to induce an expansion of a composite material made in part of expandable microspheres comprising a blowing agent contained within thermoplastic shells. The thermoplastic shells can soften (and the thickness of the thermoplastic shells can decrease) in response to an external energy directed or applied at the composite material (which can result in heat or thermal energy being transferred or transmitted to the expandable microspheres). The blowing agent within the thermoplastic shells can expand as the thermoplastic shells soften. Expansion of the blowing agent can expand the microspheres, which can, in turn, expand the composite base material serving as the bulk of the composite material. The expandable microspheres can retain their new enlarged or expanded configuration even after the external energy is no longer applied to the composite material.

Moreover, the composite material also comprises an energy absorbing constituent such as an energy absorbing dye or colorant. The energy absorbing constituent can capture or absorb a relatively harmless external energy or stimulus directed at the composite material and transform or transfer the external energy into thermal energy which can then cause the thermoplastic microspheres to expand. By designing the adjustable AIOL 100 in this manner, one or more bursts or pulses of relatively harmless energy or stimulus (e.g., light energy) can be used to induce a persistent change in the shape or size of at least part of the adjustable AIOL 100. This persistent change in the shape or size of the adjustable AIOL 100 can have a continuing effect on an optical parameter of the lens including, for example, its base power.

Figure 3A:
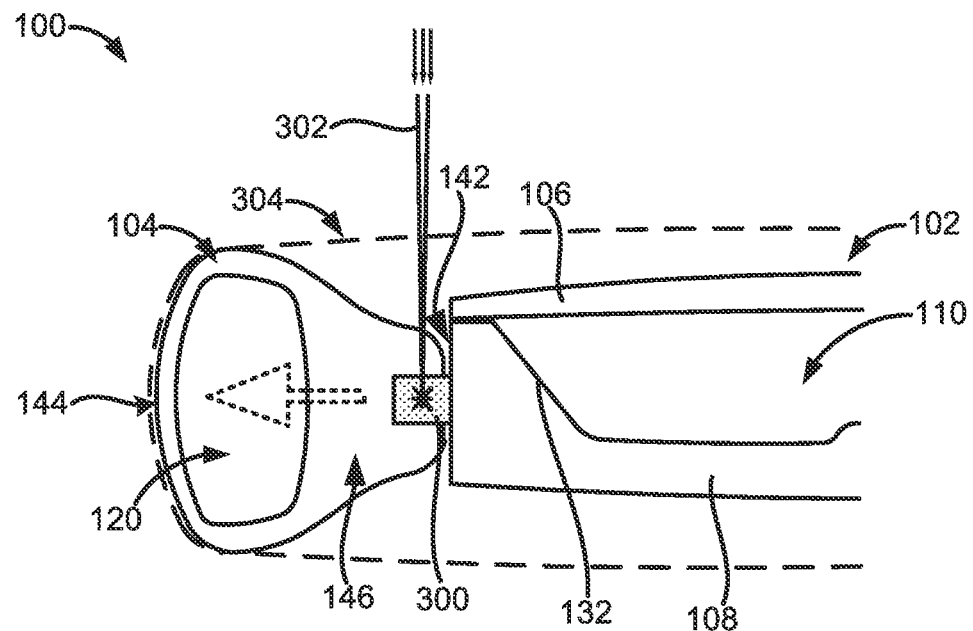
FIGS. 3A and 3B illustrate sectional views of an embodiment of the adjustable accommodating intraocular lens comprising an expandable spacer.
Figure 3B:
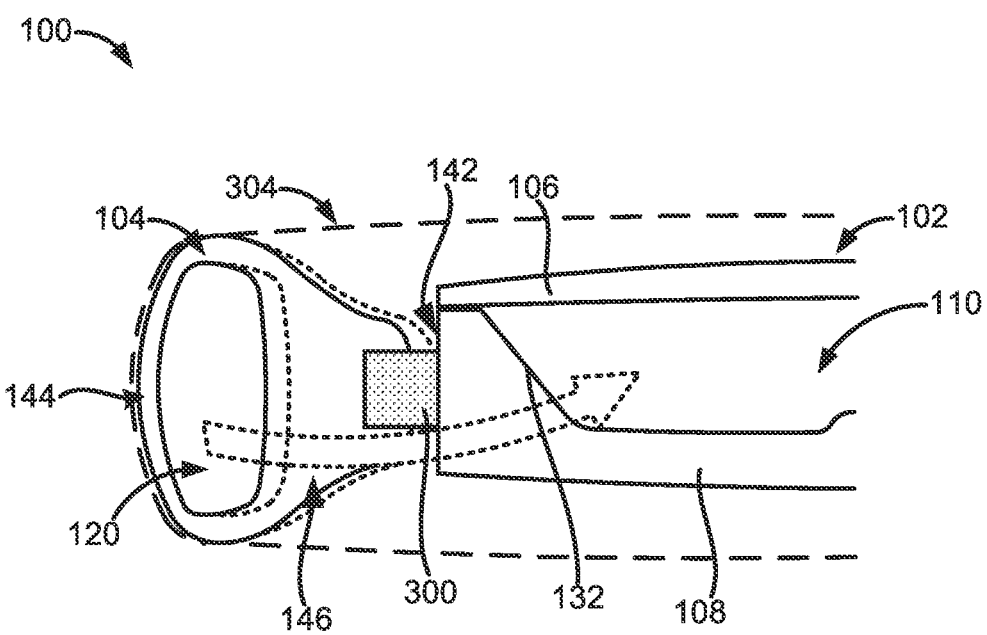

FIGS. 3A and 3B illustrate sectional views of an embodiment of the adjustable AIOL 100 comprising an expandable spacer 300 made at least in part of the composite material 200. The expandable spacer 300 can be positioned or otherwise disposed in a radially inner portion 146 of the peripheral portion 103 (e.g., a haptic 104) of the adjustable AIOL 100.

As shown in FIGS. 3A and 3B, the radially inner portion 146 of the haptic 104 can be radially thicker or bulkier than the radially outer portion 144. FIGS. 3A and 3B also illustrate the adjustable AIOL 100 as being implanted within an eye of a patient and, more specifically, as being positioned within a capsular bag 304 of the patient (shown in FIGS. 3A and 3B using broken lines). The radially outer portion 144 of the haptic 104 can come into physical contact or push against an inner surface of the capsular bag 304 when the adjustable AIOL 100 is positioned within the capsular bag 304.

As shown in FIGS. 3A and 3B, the expandable spacer 300 can be positioned partially within the radially inner portion 146 of the haptic 104. In some embodiments, at least part of the expandable spacer 300 can jut out or extend out radially inward or laterally toward the outer peripheral surface 142 of the optic portion 102. In these and other embodiments, at least part of the expandable spacer 300 can be positioned in between the haptic 104 and the optic portion 102. More specifically, the expandable spacer 300 can be positioned in between (e.g., radially in between) the optic portion 102 and the haptic fluid chamber 120.

In some embodiments, the expandable spacer 300 can be adhered to the radially inner portion 146 of the haptic 104 by being cured into place. For example, the expandable spacer 300 can be adhered to a furrow, indentation, or groove formed along the radially inner portion 146.

In other embodiments, the expandable spacer 300 can be positioned entirely within the radially inner portion 146 of the haptic 104. In some embodiments, a cavity, conduit, or other void space can be formed within the radially inner portion 146 and the expandable spacer 300 can be introduced into the cavity, conduit, or void space and cured into place.

In further embodiments, the expandable spacer 300 can refer to part of the peripheral portion 103 (e.g., the haptic 104) made of the composite material 200. For example, the expandable spacer 300 can refer to part of the radially inner portion 146 of the haptic 104 made of the composite material 200.

Although FIGS. 3A and 3B illustrate the expandable spacer 300 as having a rectangular cross-sectional profile, it is contemplated by this disclosure and it should be understood by one of ordinary skill in the art that the cross-sectional profile of the expandable spacer 300 can be substantially shaped as an oval, a circle, triangular or another polygon.

FIGS. 3A and 3B also illustrate that an external energy 302 can be directed or otherwise applied to the expandable spacer 300 to induce a shape change in the expandable spacer 300 (e.g., enlarge the expandable spacer 300) to affect an optical parameter of the adjustable AIOL 100.

In some embodiments, the external energy 302 can be light energy. More specifically, the external energy 302 can be laser light. In certain embodiments, the laser light can have a wavelength between about 488 nm to about 650 nm. The external energy 302 can be one or more bursts or pulses of laser light.

In some embodiments, the laser light can be green laser light. The green laser light can have a wavelength of between about 520 nm to about 570 nm. In one example, embodiment, the external energy 302 can be green laser light having a wavelength of about 532 nm.

For example, the laser light can be laser light emitted by an ophthalmic laser. For example, the laser light can be laser light emitted by a retinal coagulation laser.

When the external energy 302 is light energy, the energy absorbing constituents 204 can absorb or otherwise capture the light energy and convert the light energy into thermal energy to cause the expandable components 206 within the composite material 200 to expand.

As shown in FIG. 3B, the external energy 302 can cause the expandable spacer 300 to expand. Expansion of the expandable spacer 300 can cause the spacer 300 to push against the outer peripheral surface 142 of the optic portion 102. For example, the enlarged expandable spacer 300 can push against the posterior element 108 of the optic portion 102. Since the periphery of the posterior element 108 is relatively thick or bulky in between the outer peripheral surface 142 and the raised inner surface 132, the enlarged expandable spacer 300 primarily exerts a radially outward force or laterally outward force on the haptic 104.

FIG. 3B illustrates that the haptic 104 can be biased or pushed against the sides of the capsular bag 304. More specifically, the enlarged expandable spacer 300 can bias or push the radially inner portion 146 of the haptic 104 radially outward. For example, FIG. 3B illustrates the radially outward displacement of the radially inner portion 146 of the haptic 104 using solid lines to indicate the position of the radially inner portion 146 after the expansion and broken-lines to indicate the position of the radially inner portion 146 prior to the expansion. Given the limited amount of space within the capsular bag 304, this radially outward displacement of the radially inner portion 146 of the haptic 104 can cause the chamber walls of the haptic fluid chamber 120 to compress or squeeze together, thereby decreasing a volume of the haptic fluid chamber 120.

As previously discussed, both the haptic fluid chamber(s) 120 and the optic fluid chamber 110 can be filled with a fluid (e.g., silicone oil). Decreasing the volume of the haptic fluid chamber 120 can cause at least some of the fluid within the haptic fluid chamber(s) 120 to flow from the haptic fluid chamber(s) 120 into the optic fluid chamber 120. Moreover, as previously discussed, the haptic fluid chamber(s) 120 can be in fluid communication with the optic fluid chamber 120 through a plurality of fluid channels 122 (including the first pair of fluid channels 122A, the second pair of fluid channels 122B, or a combination thereof, see FIG. 1A). Although fluid flow between the haptic fluid chamber 120 and the optic fluid chamber 120 is shown in FIG. 3B using the curved arrow depicted using broken-lines, it should be understood by one of ordinary skill in the art that fluid flows from the haptic fluid chamber(s) 120 to the optic fluid chamber 120 via the plurality of fluid channels 122.

As previously discussed, the base power of the optic portion 102 can be configured to change based on an internal fluid pressure within the fluid-filled optic fluid chamber 110. The base power of the optic portion 102 can be configured to increase as fluid enters the optic fluid chamber 110 from the haptic fluid chamber(s) 120.

The optic portion 102 can also be configured to change shape in response to fluid entering the optic fluid chamber 110. In certain embodiments, the anterior element 106 of the optic portion 102 can be configured to change shape (e.g., increase its curvature) in response to the fluid entering the optic fluid chamber 110. In other embodiments, the posterior element 108 of the optic portion 102 can be configured to change shape (e.g., increase its curvature) in response to the fluid entering the optic fluid chamber 110. In further embodiments, both the anterior element 106 and the posterior element 108 can be configured to change shape in response to the fluid entering the optic fluid chamber 110. The base power of the optic portion 102 can be configured to increase in response to the shape change(s) undertaken by the anterior element 106, the posterior element 108, or a combination thereof.

As depicted in FIGS. 3A and 3B, when the expandable spacer 300 is positioned in between the optic portion 102 and the haptic fluid chamber(s) 120, applying an external energy 302 to the expandable spacer 300 can cause an interaction between the haptic(s) 104 and a capsular environment (e.g., the sides of the capsular bag 304) surrounding the haptic(s) 104. This interaction between the haptic(s) 104 and the capsular environment can result in an increase of the base power of the adjustable AIOL 100.

For example, adjusting a base power of the adjustable AIOL 100 can comprise directing or applying an external energy 302 (e.g., light energy between about 520 nm to about 570 nm) at the adjustable AIOL 100 implanted within an eye of the patient. More specifically, the external energy 302 can be applied or directed at an expandable spacer 300 made in part of the composite material 200. The expandable spacer 300 can expand in response to the application of the external energy 302. Expansion of the spacer 300 can result in the haptic(s) 104 being pushed or biased radially or laterally outward against the sides of the capsular bag 304. This can result in the walls of the haptic fluid chamber 120 being compressed or squeezed together such that a volume of the haptic fluid chamber 120 is reduced. Fluid within the haptic fluid chamber(s) 120 can then flow into the optic fluid chamber 110 in response to this reduction in the volume of the haptic fluid chamber(s) 120. The base power of the optic portion 102 can increase in response to this fluid flow into the optic fluid chamber 110.

In some embodiments, bursts or pulses of external energy 302 (e.g., light energy) directed at the expandable spacer 300 can result in an increase in the base power of the adjustable AIOL 100 by between about +0.10 D and about +0.20 D (e.g., about +0.125 D). For example, pulses of green laser light directed at the expandable spacer 300 can result in an increase in the base power of the adjustable AIOL 100 by between about +0.10 D and about +0.20 D (e.g., about +0.125 D). In some embodiments, the base power of the adjustable AIOL 100 can increase between about +1.0 D to about +5.0 D (e.g., about +2.0 D) in total in response to bursts or pulses of the external energy 302 directed at the expandable spacer 300.

Figure 4A:
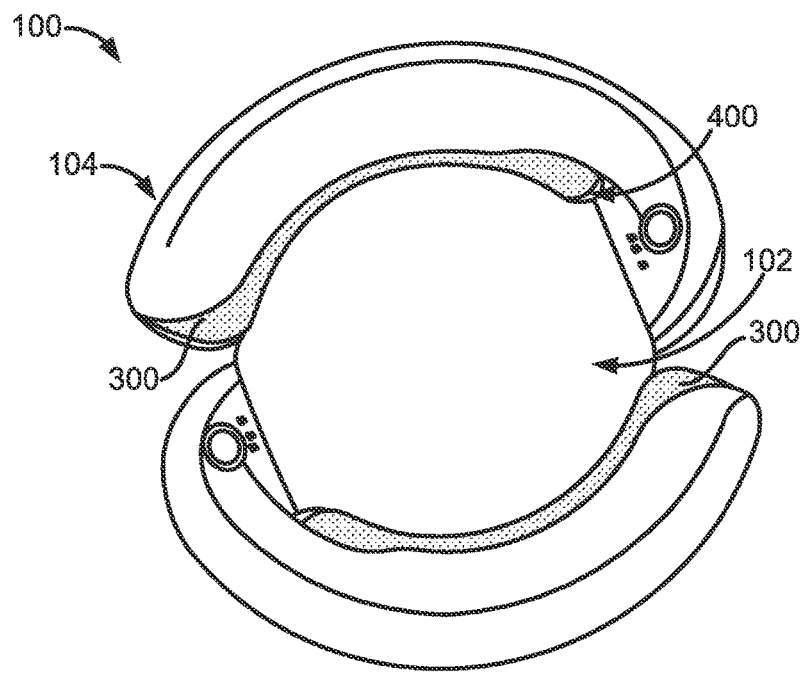
FIGS. 4A and 4B illustrate top and sectional views, respectively, of another embodiment of the adjustable accommodating intraocular lens comprising the expandable spacer extending radially inward.
Figure 4B:
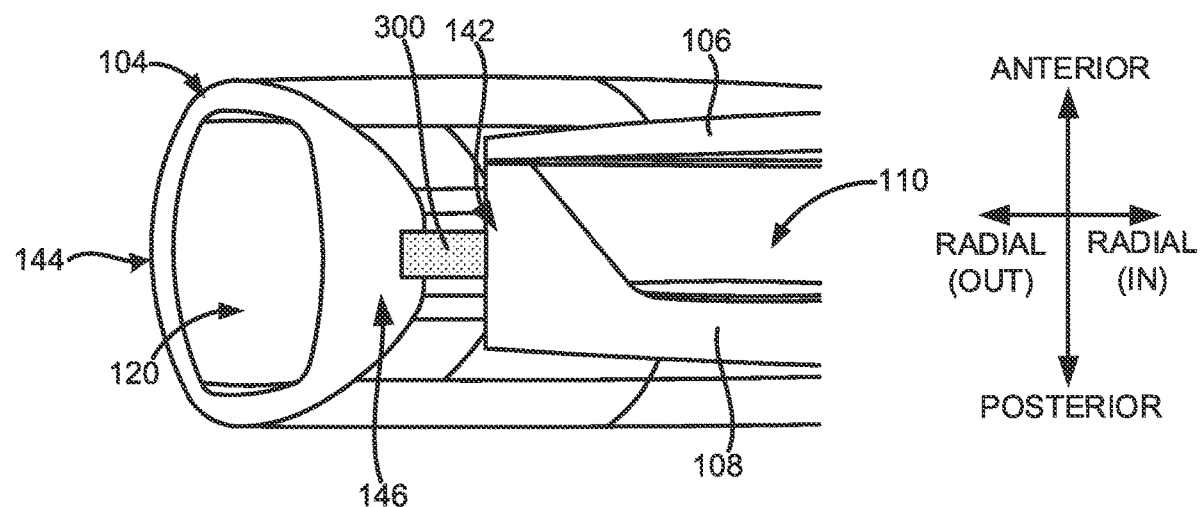

FIGS. 4A and 4B are top and sectional views, respectively, of an embodiment of the adjustable AIOL 100 comprising the expandable spacer 300 extending radially inward toward the optic portion 102 and occupying a gap space 400 in between the haptic(s) 104 and the optic portion 102.

The adjustable AIOL 100 can be implanted within the capsular bag 304 (see FIGS. 3A and 3B) of the patient when positioned according to the configuration shown in FIG. 4A. The haptics 104 of the adjustable AIOL 100 can be curved around a periphery of the optic portion 102 with the free ends of the haptics 104 on almost opposing sides of the optic portion 102.

As shown in FIG. 4A, the expandable spacer 300 can also be curved such that a radially inward portion of the expandable spacer 300 follows or matches a curvature of the optic portion 102. The expandable spacer 300 can extend along almost an entire length of each of the haptics 104.

FIG. 4B illustrates that the expandable spacer 300 can extend radially inward from the radially inner portion 146 of the haptics 104 toward the optic portion 102. In some embodiments, the expandable spacer 300 can be formed as a fin-like protrusion extending radially inward from the radially inner portion 146 of the haptics 104. In other embodiments, the expand spacer 300 can be substantially shaped as discontinuous segments of an annulus positioned, at least partly, in between the optic portion 102 and the haptics 104.

As illustrated in FIG. 4B, the expandable spacer 300 can have an anterior-to-posterior height. The anterior-to-posterior height of the expandable spacer 300 can be significantly less than the anterior-to-posterior height of the haptic 104. Moreover, the expandable spacer 300 is relatively unconstrained in the anterior and posterior directions such that any expansion of the spacer 300 primarily exerts a radially outward force or pressure on the haptics 104. Such expansion exerts relatively little force or pressure on the haptics 104 in the anterior-to-posterior direction.

In some embodiments, the expandable spacer 300 can have a spacer anterior-to-posterior height of between about 0.10 mm to about 1.00 mm. The expandable spacer 300 can also have a spacer radial width. The spacer radial width can be between about 0.50 mm to about 1.0 mm. In comparison, the haptic fluid chamber 120 can have a haptic fluid chamber anterior-to-posterior height of between about 2.0 mm to about 3.0 mm. Moreover, the haptic fluid chamber 120 can have a haptic fluid chamber radial width of between about 0.8 mm to about 1.1 mm.

Figure 5A:
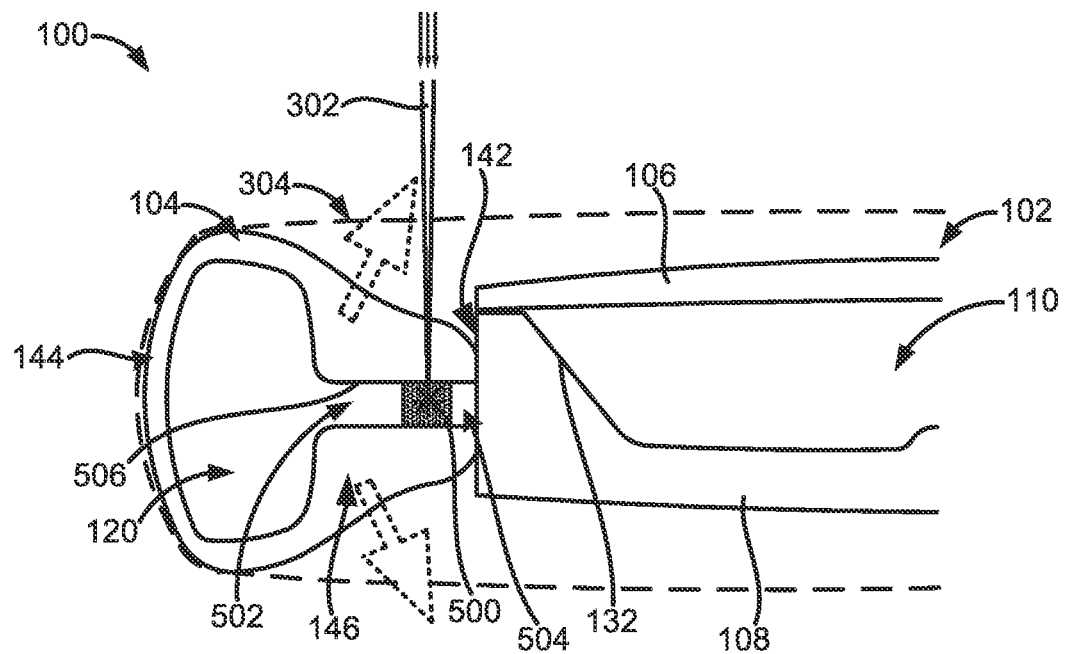
FIGS. 5A and 5B illustrate sectional views of another embodiment of the adjustable accommodating intraocular lens comprising an expandable spreader.
Figure 5B:
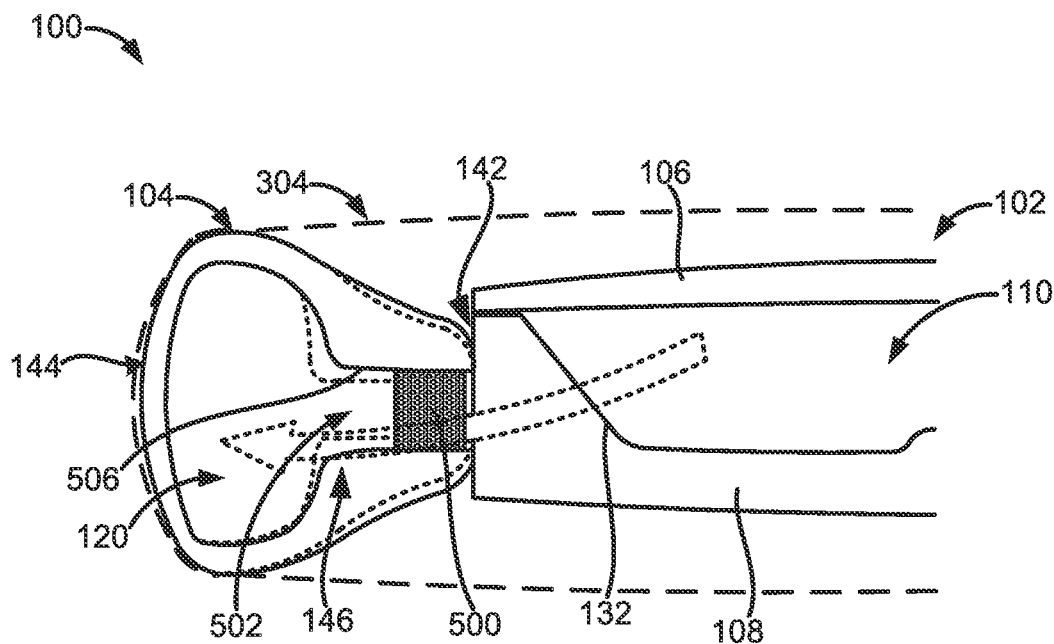

FIGS. 5A and 5B illustrate sectional views of another embodiment of the adjustable AIOL 100 comprising an expandable spreader 500 made at least in part of the composite material 200. The expandable spreader 500 can be positioned or otherwise disposed in the radially inner portion 146 of the peripheral portion 103 (e.g., the haptic(s) 104, as shown in FIGS. 5A and 5B). The radially inner portion 146 of the haptic(s) 104 can be radially thicker or bulkier than the radially outer portion 144.

As shown in FIGS. 5A and 5B, the expandable spreader 500 can be positioned within a channel 502 or opening defined within the radially inner portion 146 of the haptic 104. In some embodiments, the channel 502 or opening can extend along the entire length of the haptic 104. In other embodiments, the channel 502 or opening can extend partly along the length of the haptic 104. The channel 502 or opening can be in fluid communication with the haptic fluid chamber 120.

In some embodiments, the expandable spreader 500 can occupy all of the space within the channel 502 or opening except for a gap 504 or void space between the expandable spreader 500 and the outer peripheral surface 142 of the optic portion 102. In further embodiments, the gap 504 or void space can be replaced with the haptic material.

In other embodiments, the expandable spreader 500 can occupy at least some of the space within the channel 502 (for example, the expandable spreader 500 is positioned in a radially middle portion of the channel 502 or opening). In these embodiments, a gap 504 or void space or additional haptic material can separate (e.g., separate in a radial direction) the expandable spreader 500 from the outer peripheral surface 142 of the optic portion 102. In all such embodiments, the expandable spreader 500 can be located or positioned such that expansion of the expandable spreader 500 does not cause the radially inner portion 146 of the haptic 104 or the expander spreader 500 to substantially impinge on or push against the outer peripheral surface 142 of the optic portion 102 (thereby preventing the haptic(s) 104 from being pushed against the sides of the capsular bag 304, which can cause deformation of the haptic(s) 104 and affect the volume of the haptic fluid chamber(s) 120). For example, the expandable spreader 500 can be located or positioned such that expansion of the expandable spreader 500 does not result in the squeezing together or compression of the haptic chamber walls of the haptic fluid chamber 120 (or does not result in the reduction of the volume of the haptic fluid chamber 120).

In some embodiments, the expandable spreader 500 can be adhered to the radially inner portion 146 of the haptic 104 by being cured into place within the channel 502 or opening. For example, the expandable spreader 500 can be adhered to a location or position at the middle portion of the channel 502 or opening.

In further embodiments, the expandable spreader 500 can refer to part of the peripheral portion 103 (e.g., part of the haptic 104) made of the composite material 200. For example, the expandable spreader 500 can refer to part of the radially inner portion 146 of the haptic 104 made of the composite material 200.

Although FIGS. 5A and 5B illustrate the expandable spreader 500 as having a rectangular cross-sectional profile, it is contemplated by this disclosure and it should be understood by one of ordinary skill in the art that the cross-sectional profile of the expandable spreader 500 can be substantially shaped as an oval, a circle, triangular or other polygon.

FIGS. 5A and 5B illustrate that an external energy 302 can be directed or otherwise applied to the expandable spreader 500 to induce a shape change in the expandable spreader 500 (e.g., enlarge the expandable spreader 500) to affect an optical parameter of the adjustable AIOL 100.

In some embodiments, the external energy 302 is light energy such as a laser light. In certain embodiments, the laser light can have a wavelength between about 488 nm to about 650 nm. The external energy 302 can be one or more bursts or pulses of laser light. In some embodiments, the laser light can be green laser light.

When the external energy 302 is light energy, the energy absorbing constituents 204 can absorb or otherwise capture the light energy and convert the light energy into thermal energy to cause the expandable components 206 within the composite material 200 to expand.

As shown in FIG. 5B, the external energy 302 can cause the expandable spreader 500 to expand. Expansion of the expandable spreader 500 can cause the spreader 500 to push against channel walls 506 of the channel 502 defined within the radially inner portion 146 of the haptic 104.

FIG. 5B illustrates that the enlarged spreader 500 can expand or spread apart the channel walls 506 to expand or spread apart the channel 502. Moreover, the enlarged spreader 500 can also deform the chamber walls of the haptic fluid chamber 120 by spreading apart at least some of the chamber walls, thereby enlarging the volume of the haptic fluid chamber 120.

The enlarged expandable spreader 500 can bias or push apart the channel walls 506 of the channel 502, at least in an anterior-to-posterior direction. This can result in an increase in the volume of the haptic fluid chamber 120. For example, FIG. 5B illustrates the spread apart channel walls 506 and haptic chamber walls using solid lines and the position of the channel walls 506 and haptic chamber walls prior to expansion using broken-lines. FIG. 5B also illustrates that the gap 504 or void space in between the spreader 500 and the optic portion 102 allows the spreader 500 to expand or increase in size without causing the spreader 500 to impinge on or push against the outer peripheral surface 142 of the optic portion 102 (thereby preventing the haptic(s) 104 from being pushed against the sides of the capsular bag 304, which can cause deformation of the haptic(s) 104 and affect the volume of the haptic fluid chamber(s) 120). In other embodiments, additional haptic material can separate the spreader 500 from the outer peripheral surface 142 of the optic portion 102 such that expansion of the spreader 500 only spreads apart the channel walls 506 and chamber walls and does not cause the radially outer portion 144 of the haptic(s) 104 to push against the sides of the capsular bag 304.

As previously discussed, both the haptic fluid chamber(s) 120 and the optic fluid chamber 110 can be filled with a fluid (e.g., silicone oil). Increasing the volume of the haptic fluid chamber 120 can cause at least some of the fluid within the optic fluid chamber 110 to flow from the optic fluid chamber 110 into the haptic fluid chamber(s) 120. Moreover, as previously discussed, the haptic fluid chamber(s) 120 can be in fluid communication with the optic fluid chamber 120 through a plurality of fluid channels 122 (including the first pair of fluid channels 122A, the second pair of fluid channels 122B, or a combination thereof, see FIG. 1A). Although fluid flow between the haptic fluid chamber 120 and the optic fluid chamber 120 is shown in FIG. 5B using the curved arrow depicted using broken-lines, it should be understood by one of ordinary skill in the art that fluid flows from the optic fluid chamber 110 to the haptic fluid chamber(s) 120 via the plurality of fluid channels 122.

As previously discussed, the base power of the optic portion 102 can be configured to change based on an internal fluid pressure within the fluid-filled optic fluid chamber 110. The base power of the optic portion 102 can be configured to decrease as fluid enters the haptic fluid chamber(s) 120 from the optic fluid chamber 110.

The optic portion 102 can also be configured to change shape in response to fluid exiting the optic fluid chamber 110. In certain embodiments, the anterior element 106 of the optic portion 102 can be configured to change shape (e.g., decrease its curvature) in response to the fluid exiting the optic fluid chamber 110. In other embodiments, the posterior element 108 of the optic portion 102 can be configured to change shape (e.g., decrease its curvature) in response to the fluid exiting the optic fluid chamber 110. In further embodiments, both the anterior element 106 and the posterior element 108 can be configured to change shape in response to the fluid exiting the optic fluid chamber 110. The base power of the optic portion 102 can be configured to decrease in response to the shape change(s) undertaken by the anterior element 106, the posterior element 108, or a combination thereof.

As depicted in FIGS. 5A and 5B, applying an external energy 302 to the expandable spreader 500 (e.g., when the expandable spreader 500 is positioned within a channel 502 or opening defined within the radially inner portion 146 of the haptic(s) 104) can cause the volume of the haptic fluid chamber(s) 120 to increase. This increase in the volume of the haptic fluid chamber(s) 120 can draw fluid out of the optic fluid chamber 110 and cause a decrease in the base power of the adjustable AIOL 100.

For example, a method of decreasing a base power of the adjustable AIOL 100 can comprise directing or applying an external energy 302 (e.g., light energy between about 520 nm to about 570 nm) at an expandable spreader 500 embedded within the adjustable AIOL 100 implanted within an eye of the patient. More specifically, the external energy 302 can be applied or directed at an expandable spreader 500 made in part of the composite material 200. The expandable spreader 500 can expand in response to the application of the external energy 302. Expansion of the spreader 500 can result in the volume of the haptic fluid chamber(s) 120 being enlarged. Fluid within the optic fluid chamber 110 can then flow into the haptic fluid chamber(s) 110 in response to this increase in the volume of the haptic fluid chamber(s) 120. The base power of the optic portion 102 can decrease in response to this fluid flow out of the optic fluid chamber 110.

In some embodiments, bursts or pulses of external energy 302 (e.g., light energy) directed at the expandable spreader 500 can result in a decrease in the base power of the adjustable AIOL 100 by between about −0.10 D and about −0.20 D (e.g., about −0.125 D). For example, pulses of green laser light directed at the expandable spreader 500 can result in a decrease in the base power of the adjustable AIOL 100 by between about −0.10 D and about −0.20 D (e.g., about −0.125 D). In some embodiments, the base power of the adjustable AIOL 100 can decrease between about −1.0 D to about −5.0 D (e.g., about −2.0 D) in total in response to bursts or pulses of the external energy 302 directed at the expandable spreader 500.

Figure 6:
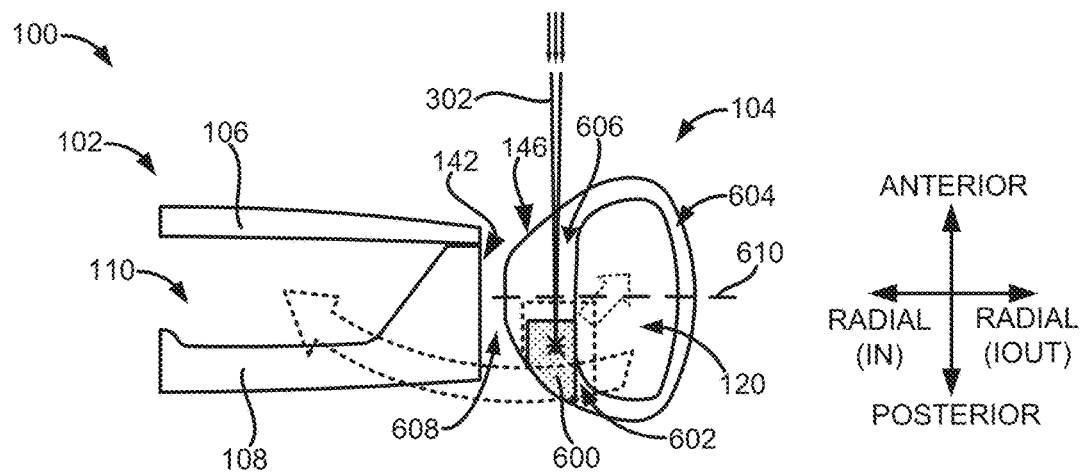
FIG. 6 illustrates a sectional view of another embodiment of the adjustable accommodating intraocular lens comprising an expandable protuberance.

FIG. 6 illustrates a sectional view of another embodiment of the adjustable AIOL 100 comprising an expandable protuberance 600 made at least in part of the composite material 200. The expandable protuberance 600 can be positioned or otherwise disposed along part of the radially inner portion 146 of the peripheral portion 103 (e.g., the one or more haptics 104) of the adjustable AIOL 100.

As shown in FIG. 6, the haptic 104 (e.g., any of the first haptic 104A or the second haptic 104B) can comprise haptic chamber walls surrounding the haptic fluid chamber 120. For example, the haptic chamber walls can comprise a radially inner wall 602 and radially outer wall 604. The haptic fluid chamber 120 can be defined in part by the radially inner wall 602 and the radially outer wall 604.

The expandable protuberance 600 can be positioned or otherwise disposed along part of the radially inner wall 602 of the haptic 104. More specifically, the expandable protuberance 600 can be positioned or otherwise disposed or affixed along a radially outermost portion 606 of the radially inner wall 602 of the haptic 104.

In some embodiments, the adjustable AIOL 100 can be designed such that a gap or void space 608 radially separates the radially inner wall 602 of the haptic 104 from the outer peripheral surface 142 of the optic portion 102. This can ensure that neither the expandable protuberance 600 nor the radially inner wall 602 impinges or pushes against the outer peripheral surface 142 of the optic portion 102 when the expandable protuberance 600 expands (thereby preventing the haptic(s) 104 from being pushed against the sides of the capsular bag 304, which can cause deformation of the haptic(s) 104 and affect the volume of the haptic fluid chamber(s) 120). As previously discussed, when the radially inner portion 146 of the haptic 104 pushes against the outer peripheral surface 142 of the optic portion 102, the haptic chamber walls can compress or squeeze together as a result of the radially outer wall 604 of the haptic 104 pressing against the sides of the capsular bag 304 of the patient. In other embodiments, the adjustable AIOL 100 can be designed such that the radially inner wall 602 of the haptic 104 continuously rests against the outer peripheral surface 142 of the optic portion 102 or intermittently rests against the outer peripheral surface 142 of the optic portion 102.

In some embodiments, for example, as shown in FIG. 6, the entire expandable protuberance 600 can be positioned below (or above) a halfway line or haptic midline 610. The halfway line or haptic midline 610 can bisect the anterior-to-posterior height of the haptic 104 In these embodiments, no part of the expandable protuberance 600, in an unexpanded state, can extend beyond the haptic midline 610. An anterior-to-posterior height of the expandable protuberance 600 can be less than the anterior-to-posterior height of the radially inner wall 602.

In some embodiments, the expandable protuberance 600 can be adhered to the radially inner portion 146 (e.g., the radially inner wall 602) of the haptic 104 by being cured into place. For example, the expandable protuberance 600 can be adhered to a cavity, furrow, or groove formed along the radially outermost portion 606 of the radially inner wall 602. In these instances, the expandable protuberance 600 can take up or occupy less than half the anterior-to-posterior height of the radially inner wall 602.

In further embodiments, the expandable protuberance 600 can refer to part of the radially inner portion 146 (e.g., part of the radially inner wall 602) made of the composite material 200. For example, the expandable protuberance 600 can refer to a part of the radially outermost portion 606 of the radially inner wall 602 made of the composite material 200.

Although FIG. 6 illustrates the cross-sectional profile of the expandable protuberance 600 as having primarily straight edges and corners, it is contemplated by this disclosure and it should be understood by one of ordinary skill in the art that the cross-sectional profile of the expandable protuberance 600 can also have rounded or curved edges and corners.

FIG. 6 also illustrate that an external energy 302 can be directed or otherwise applied to the expandable protuberance 600 to induce a shape change in the expandable protuberance 600 (e.g., enlarge the expandable protuberance 600) to affect an optical parameter of the adjustable AIOL 100.

The external energy 302 can be the same external energy 302 as previously disclosed. For example, when the external energy 302 is light energy, the energy absorbing constituents 204 can absorb or otherwise capture the light energy and convert the light energy into thermal energy to cause the expandable components 206 within the composite material 200 to expand.

As shown in FIG. 6, the external energy 302 can cause the expandable protuberance 600 to expand (as depicted by the enlarged protuberance 600 shown in broken lines). Expansion of the expandable protuberance 600 can cause the protuberance 600 to encroach, extend, or otherwise grow into the fluid-filled haptic fluid chamber 120. This can cause fluid within the haptic fluid chamber 120 to be displaced or pushed into the optic fluid chamber 110 (through the plurality of fluid channels 122). Moreover, when the protuberance 600 expands and part of the protuberance 600 encroaches, extends, or grows into the haptic fluid chamber 120, the fluid carrying capacity or the available volume of the haptic fluid chamber 120 can decrease.

As previously discussed, both the haptic fluid chamber(s) 120 and the optic fluid chamber 110 can be filled with a fluid (e.g., silicone oil). Reducing the fluid carrying capacity or the available volume of the haptic fluid chamber 120 can cause at least some of the fluid within the haptic fluid chamber(s) 120 to flow from the haptic fluid chamber(s) 120 into the optic fluid chamber 120, and remain in the optic fluid chamber 120. Although fluid flow between the haptic fluid chamber 120 and the optic fluid chamber 120 is shown in FIG. 6 using the curved arrow depicted using brokenlines, it should be understood by one of ordinary skill in the art that fluid flows from the haptic fluid chamber(s) 120 to the optic fluid chamber 120 via the plurality of fluid channels 122.

As previously discussed, the base power of the optic portion 102 can be configured to change based on an internal fluid pressure within the fluid-filled optic fluid chamber 110. The base power of the optic portion 102 can be configured to increase as fluid enters the optic fluid chamber 110 from the haptic fluid chamber(s) 120.

The optic portion 102 can also be configured to change shape in response to fluid entering the optic fluid chamber 110. In certain embodiments, the anterior element 106 of the optic portion 102 can be configured to change shape (e.g., increase its curvature) in response to the fluid entering the optic fluid chamber 110. In other embodiments, the posterior element 108 of the optic portion 102 can be configured to change shape (e.g., increase its curvature) in response to the fluid entering the optic fluid chamber 110. In further embodiments, both the anterior element 106 and the posterior element 108 can be configured to change shape in response to the fluid entering the optic fluid chamber 110. The base power of the optic portion 102 can be configured to increase in response to the shape change(s) undertaken by the anterior element 106, the posterior element 108, or a combination thereof.

In some embodiments, bursts or pulses of external energy 302 (e.g., light energy) directed at the expandable protuberance 600 can result in an increase in the base power of the adjustable AIOL 100 by between about +0.10 D and about +0.20 D (e.g., about +0.125 D). For example, pulses of green laser light directed at the expandable protuberance 600 can result in an increase in the base power of the adjustable AIOL 100 by between about +0.10 D and about +0.20 D (e.g., about +0.125 D). In some embodiments, the base power of the adjustable AIOL 100 can increase between about +1.0 D to about +5.0 D (e.g., about +2.0 D) in total in response to bursts or pulses of the external energy 302 directed at the expandable protuberance 600.

Figure 7A:
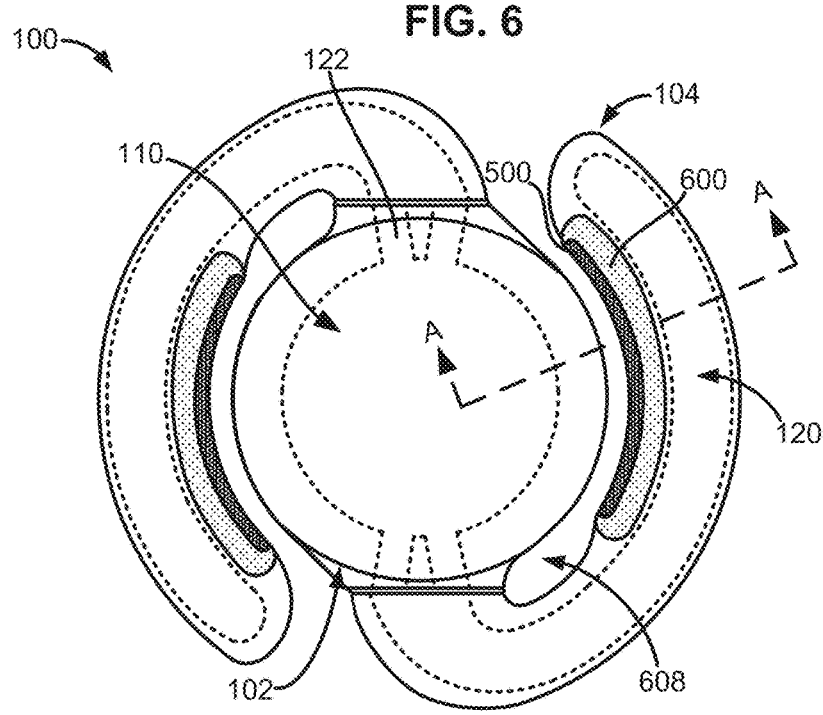
FIGS. 7A and 7B illustrate top and sectional views, respectively, of another embodiment of the adjustable accommodating intraocular lens comprising both an expandable spreader and an expandable protuberance.
Figure 7B:
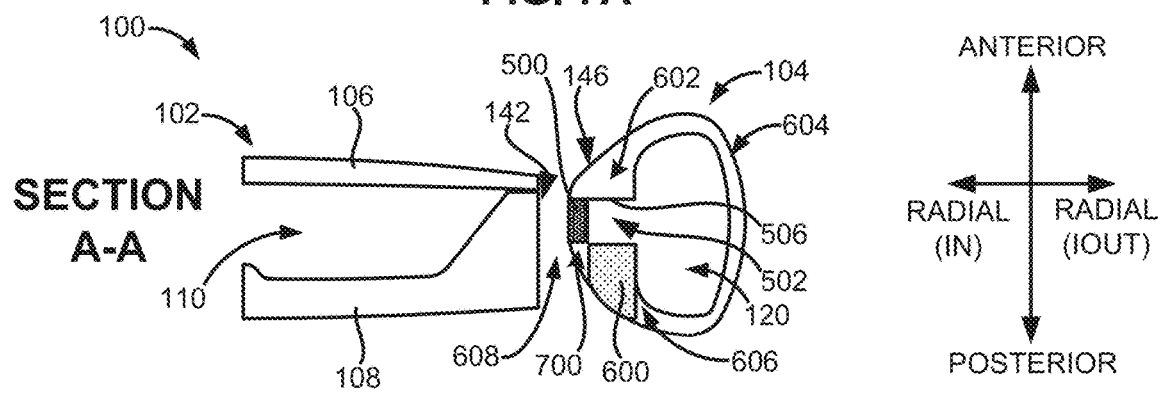

FIGS. 7A and 7B illustrate top and sectional views, respectively, of another embodiment of the adjustable AIOL 100 comprising both an expandable spreader 500 and an expandable protuberance 600 making up at least part of each of the haptics 104. For example, as shown in FIG. 7A, a first haptic portion made of the expandable spreader 500 can be positioned or adhered to one part of the haptic chamber wall and a second haptic portion made of the expandable protuberance 600 can be positioned or adhered to another part of the same haptic chamber wall.

In some embodiments, the first haptic portion (e.g., the expandable spreader 500) can be made in part of a first composite material, or a first type of the composite material 200 shown in FIG. 2A, and the second haptic portion (e.g., the expandable protuberance 600) can be made in part of a second composite material, or a second type of the composite material 200 shown in FIG. 2A.

In some embodiments, the first composite material can be made in part of a first energy absorbing constituent (e.g., a first type of the energy absorbing constituent 204 shown in FIG. 2A) and the second composite material can be made in part of a second energy absorbing constituent (e.g., a second type of the energy absorbing constituent 204 shown in FIG. 2A). For example, the first composite material can be made in part of Disperse Red 1 dye and the second composite material can be made in part of graphitized carbon black. The first energy absorbing constituent can have or exhibit a first color (e.g., the Disperse Red 1 dye can have or exhibit a red color) and the second energy absorbing constituent can have or exhibit a second color (e.g., the graphitized carbon black can have or exhibit a black color) different from the first color. Also, as another example, the first energy absorbing constituent can be an azo dye having a first color (e.g., Disperse Red 1 dye) and the second energy absorbing constituent can be another azo dye having a second color (e.g., Disperse Orange 1 dye). This difference in color can allow a clinician or another medical professional to visually differentiate between the two haptic portions.

In certain embodiments, the first composite material made in part of the first energy absorbing constituent can expand in response to a first type of external energy (e.g., light energy between 520 nm to 540 nm) directed at the first composite material and the second composite material made in part of the second energy absorbing constituent can expand in response to a second type of external energy (e.g., light energy between 600 nm and 650 nm) directed at the second energy absorbing constituent. In these and other embodiments, the first energy absorbing constituent can have or exhibit a first color (e.g., red color) and the second energy absorbing constituent can have or exhibit a second color (e.g., an orange or blue color) different from the first color.

In other embodiments, the first composite material and the second composite material can be made in part of the same energy absorbing constituents but comprise different amounts or weight percentages of such constituents. In other embodiments, the first composite material and the second composite material can be made in part of the same energy absorbing constituents but comprise different amounts or weight percentages of expandable components 206.

As shown in FIG. 7A, the first haptic portion made in part of the first composite material can be positioned or located radially offset from the second haptic portion made in part of the second composite material. For example, the expandable spreader 500 can be positioned radially offset from the expandable protuberance 600 on each of the haptics 104. More specifically, a radially innermost portion of the haptic 104 can be made in part of the expandable spreader 500 and an adjoining portion of the haptic radially outward from the expandable spreader 500 can be made in part of the expandable protuberance 600.

Also, as shown in FIG. 7A, the expandable spreader 500 can extend along part of a length of the haptic 104. Moreover, the expandable protuberance 600 can also extend along part of the length of the haptic 104.

FIG. 7B illustrates that the same radially inner wall 602 of the haptic 104 can comprise both an expandable spreader 500 and an expandable protuberance 600. In the embodiment shown in FIG. 7B, the expandable spreader 500 can be made in part of a first composite material (e.g., a composite material 200 comprising a first energy absorbing colorant) and the expandable protuberance 600 can be made in part of a second composite material (e.g., a composite material 200 comprising a second energy absorbing colorant). The difference in the color of the energy absorbing colorants can allow a clinician or another medical professional to more easily distinguish the expandable spreader 500 and the expandable protuberance 600. In other embodiments (for example, as depicted in FIG. 9B), the expandable spreader 500 and the expandable protuberance 600 can be made of the same composite material 200.

The expandable spreader 500 can be positioned within a channel 502 or opening defined within the radially inner wall 602. The channel 502 or opening can be in fluid communication with the haptic fluid chamber 120.

In some embodiments, the expandable spreader 500 can occupy a radially innermost portion 700 of the radially inner wall 602 of the haptic 104. In these embodiments, the expandable spreader 500 can also occupy or be disposed at a radially innermost end of the channel 502. In further embodiments, the expander spreader 500 can refer to part of a haptic chamber wall of the haptic 104 made of the composite material 200. For example, in these embodiments, the expander spread 500 can refer to part of the radially innermost portion 700 of the radially inner wall 602 of the haptic 104 made of the composite material 200.

As shown in FIG. 7B, a void space 608 or gap can separate the radially innermost portion 700 of the radially inner wall 602 of the haptic 104 from the outer peripheral surface 142 of the optic portion 102. This can allow the expandable spreader 500 to expand without impinging on or pushing up against the outer peripheral surface 142 of the optic portion 102.

As further shown in FIG. 7B, the expandable protuberance 600 can be positioned or otherwise disposed or affixed along a radially outermost portion 606 of the radially inner wall 602 of the haptic 104. In certain embodiments, the expandable protuberance 600 can refer to part of the haptic chamber wall made of the composite material 200. For example, the expandable protuberance 600 can refer to part of the radially outermost portion 606 of the radially inner wall 602 of the haptic 104 made of the composite material 200.

External energy 302 directed or otherwise applied to the expander spreader 500 positioned along the haptic chamber wall (e.g., positioned along the radially innermost portion 700 of the radially inner wall 602 of the haptic 104) can cause the expandable spreader 500 to expand. Expansion of the expandable spreader 500 can cause the spreader 500 to push against the channel walls 506 of the channel 502 and enlarge at least one of the channel 502 and the haptic fluid chamber 120. This can cause the volume of the haptic fluid chamber(s) 120 to increase. This can then draw fluid out of the optic fluid chamber 110 into the haptic fluid chamber(s) 120 (via the fluid channels 122) and cause a decrease in the base power of the adjustable AIOL 100 (e.g., a decrease between about −0.10 D and −0.20 D).

The same external energy 302 or another type of external energy 302 (e.g., light energy of another wavelength) can also be directed or otherwise applied to the expandable protuberance 600 positioned along the haptic chamber wall (e.g., positioned along the radially outermost portion 606 of the radially inner wall 602 of the haptic 104). The external energy can cause the expandable protuberance 600 to expand. Expansion of the expandable spreader 500 can cause the protuberance 600 to encroach, extend, or otherwise grow into the fluid-filled haptic fluid chamber 120. This can cause fluid within the haptic fluid chamber 120 to be displaced or pushed into the optic fluid chamber 110 (through the plurality of fluid channels 122). Bursts or pulses of external energy 302 (e.g., light energy) directed at the expandable protuberance 600 can result in an increase in base power of the adjustable AIOL 100 by between about +0.10 D and +0.20 D.

Figure 8:
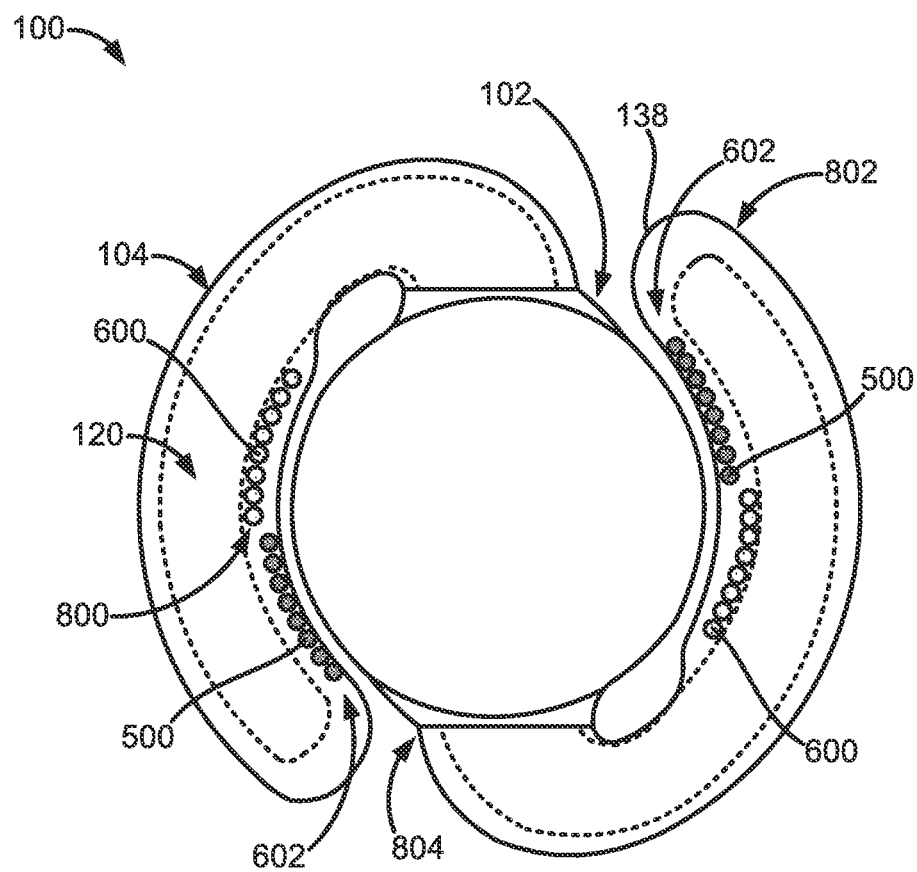
FIG. 8 illustrates a top plan view of another embodiment of the adjustable accommodating intraocular lens comprising both expandable spreaders and expandable protuberances implemented as discrete components along the haptics.

FIG. 8 illustrates a top plan view of another embodiment of the adjustable AIOL 100 comprising both expandable spreaders 500 and expandable protuberances 600 implemented as discrete components 800 along the haptics 104. In alternative embodiments, at least one of the expandable spreaders 500 and the expandable protuberances 600 can be replaced with expandable spacers 300 (see FIGS. 3A and 3B).

In some embodiments, the expandable spreaders 500 can occupy or be positioned along a radially innermost portion 700 (see, FIG. 7B) of the radially inner wall 602 of the haptic(s) 104. The expandable protuberances 600 can occupy or be positioned along a radially outermost portion 606 (see, FIG. 6) of the radially inner wall 602 of the haptic(s) 104.

At least one of the expandable spreaders 500 and the expandable protuberances 600 can be implemented or configured as discrete components 800 visually perceptible to a clinician or another medical professional responsible for adjusting the adjustable AIOL 100 when the adjustable AIOL 100 is implanted within an eye of a patient.

The discrete components 800 can refer to a shape or configuration of the expandable spreaders 500, the expandable protuberances 600, or a combination thereof. In some embodiments, the discrete components 800 can have a circular profile when viewed from the top down or when viewed in an anterior to posterior direction. In these embodiments, each of the discrete components 800 can be shaped substantially as a cylinder. In other embodiments not shown in the figures, the discrete components 800 can have an oval profile, a rectangular profile, a triangular profile, a diamond or rhombus profile, a star profile, any other polygonal profile, or a combination thereof when viewed from the top down or when viewed in an anterior to posterior direction. The discrete components 800 can be spaced close apart or each of the discrete components 800 can be separated from one another by portions of the haptic material.

Moreover, as shown in FIG. 8, a portion or segment of one haptic 104 can comprise the expandable spreaders 500 and another portion or segment of the same haptic 104 can comprise the expandable protuberances 600. For example, a distal segment 802 of each of the haptics 104 (e.g., a segment 802 closer to the closed free end 138 of the haptics 104) can comprise the expandable spreaders 500 and a proximal segment 804 of each of the haptics 104 (e.g., a segment 804 closer to the optic portion 102) can comprise the expandable protuberances 600. As shown in FIG. 8, the expandable protuberances, implemented as discrete components 800, can be radially offset or radially separated from the expandable spreaders 500, also implemented as discrete components 800.

Designing or otherwise configuring at least one of the expandable spreaders 500 and the expandable protuberances 600 as discrete components 800 can allow a clinician or medical professional to fine tune the adjustment of the adjustable AIOL 100. For example, the clinician or medical professional can direct the external energy 302 at one of the discrete components 800 to either increase the base power of the adjustable AIOL 100 (when the discrete component 800 is an expandable protuberance 600) or decrease the base power of the adjustable AIOL 100 (when the discrete component 800 is an expandable spreader 500) by a set amount. More specifically, in certain embodiments, the discrete components 800 can be sized, shaped, or located to allow bursts or pulses of the external energy 302 applied to each of the discrete components 800 to adjust an optical parameter (e.g., a base power) of the adjustable AIOL 100 by a predetermined or preset amount. For example, bursts or pulses of the external energy 302 applied to or directed at each of the discrete components 800 can cause a change in the base power by about ±0.10 D and ±0.20 D (e.g., about ±0.125 D).

Moreover, in this example, the clinician or medical professional can also direct further bursts or pulses of the external energy 302 at the same discrete component 800 to further increase or decrease the base power of the adjustable AIOL 100 or direct further bursts or pulses of the external energy 302 at a different discrete component 800 to undo or negate a previous adjustment (for example, to decrease the base power after an increase of the base power has been induced).

Although FIG. 8 illustrates the haptic(s) 104 comprising both the expandable spreaders 500 and the expandable protuberances 600 (configured as discrete components 800), it is contemplated by this disclosure and it should be understood by one of ordinary skill in the art that each of the haptics 104 can also comprise only the expandable spreaders 500 or only the expandable protuberances 600 as discrete components 800.

As shown in FIGS. 7A, 7B, and 8, the adjustable AIOL 100 can be configured such that a base power of the adjustable AIOL 100 can be adjusted in a first manner (e.g., increasing the base power) by directing or otherwise applying an external energy 302 at a first portion of the haptic 104 made in part of the composite material 200. Moreover, the base power of the adjustable AIOL 100 can be adjusted in a second manner (e.g., decreasing the base power) by directing or otherwise applying additional bursts or pulses of the external energy 302 at a second portion of the same or different haptic 104 made in part of the composite material 200. In some embodiments, the composite material 200 used to make the first portion of the haptic 104 can be or exhibit a different color than the composite material 200 used to make the second portion of the haptic 104 as a result of differences in the energy absorbing constituents 204 making up the composite materials 200.

Figure 9A:
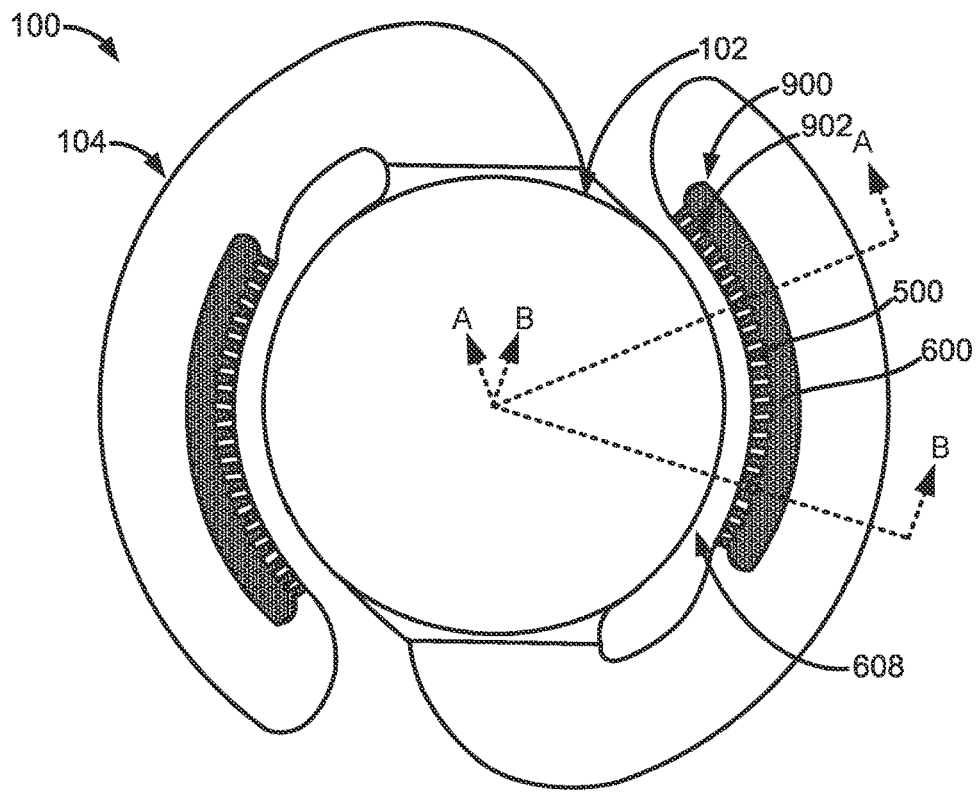
FIG. 9A illustrates a top plan view of another embodiment of the adjustable accommodating intraocular lens comprising both expandable spreaders and expandable protuberances arranged in a visually perceptible pattern.
Figure 9B:
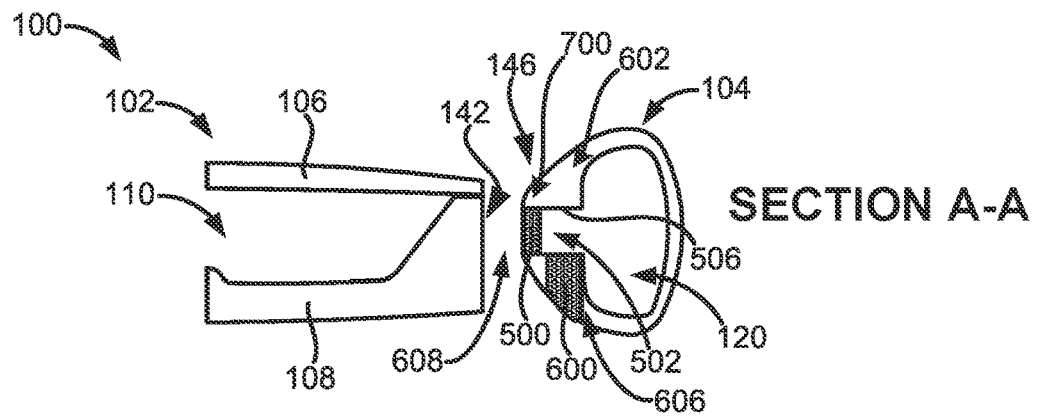
FIG. 9B illustrates a sectional view of the embodiment of the adjustable accommodating intraocular lens shown in FIG. 9A taken along cross-section A-A.

FIG. 9A illustrates a top plan view of another embodiment of the adjustable AIOL 100 comprising both expandable spreaders 500 and expandable protuberances 600 arranged in a visually perceptible pattern 900. The visually perceptible pattern 900 can allow a clinician or medical professional responsible for post-operatively adjusting the adjustable AIOL 100 to distinguish between the expandable spreaders 500 and the expandable protuberances 600, especially when the expandable spreaders 500 and the expandable protuberances 600 are made from the same composite material 200 having the same color (as shown in FIG. 9A). This can allow the clinician or medical professional to more easily determine where to direct or apply the external energy 302 on the adjustable AIOL 100 in order to adjust an optical parameter of the adjustable AIOL 100.

Figure 9C:
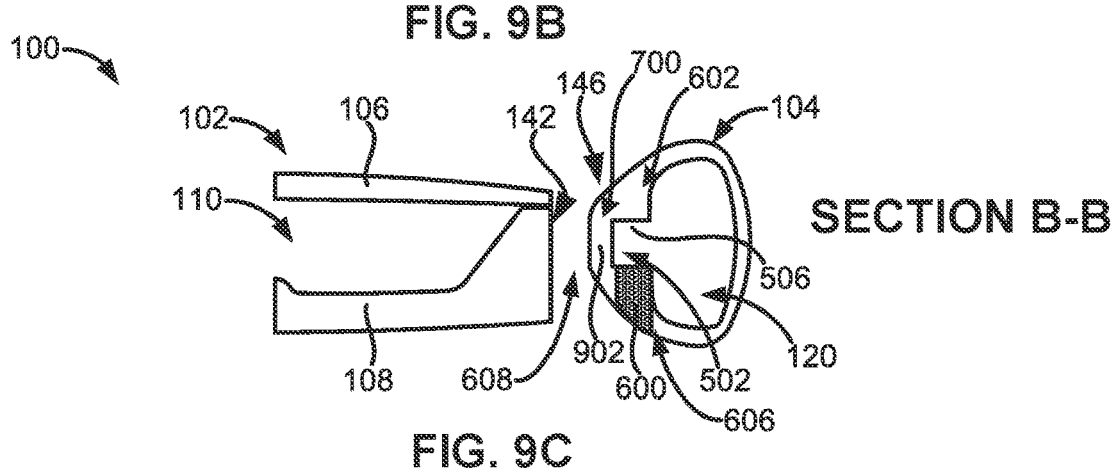
FIG. 9C illustrates a sectional view of the embodiment of the adjustable accommodating intraocular lens shown in FIG. 9A taken along cross-section B-B.

As shown in FIG. 9A-9C, the visually perceptible pattern 900 can include both a continuous curved segment of the expandable protuberance 600 and spaced-apart branches or finger-shaped segments of the expandable spreaders 500 extending radially inward from the continuous curved segment. FIG. 9A also illustrates that the branches or finger-shaped segments of the expandable protuberance 600 can be separated from one another by portions of haptic material 902. The haptic material 902 can be the same haptic material used to construct the remainder of the haptic(s) 104. For example, the visually perceptible pattern 900 can be a comb-shaped pattern. In other embodiments, the visually perceptible pattern 900 can be a wave pattern, a chained-triangular pattern, a zig-zag pattern, or a combination thereof.

For example, a clinician or another medical professional can direct or otherwise apply the external energy 302 at the spaced-apart branches or finger-shaped segments to expand the expandable spreaders 500 in order to decrease the base power of the adjustable AIOL 100. The clinician or medical professional can also direct or otherwise apply the external energy 302 at the expandable protuberance 600 shaped as the curved portion positioned radially outward of the spaced-apart branches or finger-shaped segments to expand the expandable protuberance 600 in order to increase the base power of the adjustable AIOL 100.

FIG. 9B illustrates a sectional view of the embodiment of the adjustable AIOL 100 shown in FIG. 9A taken along cross-section A-A. As shown in FIG. 9B, this section of the haptic 104 can comprise both the expandable spreader 500 and the expandable protuberance 600 adhered, formed, or otherwise positioned along the radially inner wall 602. The expandable spreaders 500 can be positioned along the radially innermost portion 700 of the radially inner wall 602 or at a radially innermost end of a channel 502 defined along the radially inner wall 602. The expandable protuberance 600 can be positioned along a radially outermost portion 606 of the radially inner wall 602 of the haptic 104. The expandable protuberance 600 can be positioned underneath or further posterior of the expandable spreader 500. Moreover, the adjustable AIOL 100 can be configured such that a void space 608 or gap separates the radially inner wall 602 of the haptic 104 from the outer peripheral surface 142 of the optic portion 102 such that expansion of the expandable spreader 500 does not cause any part of the haptic 104 to substantially impinge on or push up against the outer peripheral surface 142 of the optic portion 102 (thereby preventing the haptic(s) 104 from being pushed against the sides of the capsular bag 304, which can cause deformation of the haptic(s) 104 and affect the volume of the haptic fluid chamber(s) 120).

FIG. 9C illustrates a sectional view of the embodiment of the adjustable AIOL 100 shown in FIG. 9A taken along cross-section B-B. As shown in FIG. 9C, this section of the haptic 104 can comprise only the expandable protuberance 600 adhered, formed, or otherwise positioned along the radially inner wall 602. The expandable protuberance 600 can be positioned along a radially outermost portion 606 of the radially inner wall 602 of the haptic 104. The remainder of the radially inner wall 602 can be made of the same haptic material 902 used to construct the rest of the haptic 104.

The visually perceptible pattern 900 can allow a clinician or medical professional to more easily determine where to direct or apply the external energy 302 on the adjustable AIOL 100 in order to adjust an optical parameter of the adjustable AIOL 100. This can be useful when both the expandable spreaders 500 and the expandable protuberances 600 are made of the same composite material 200 having or exhibiting the same color. The clinician or medical professional can direct or otherwise apply the external energy 302 exclusively at the expandable protuberance 600 shaped as the curved portion to expand the expandable protuberance 600 in order to increase the base power of the adjustable AIOL 100. The clinician or medical professional can also direct or otherwise apply the external energy 302 exclusively at the branches or finger-shaped portion to expand the expandable spreaders 500 in order to decrease the base power of the adjustable AIOL 100.

One technical problem faced by the applicants is how to integrate the composite material with the rest of the adjustable AIOL without interfering with the optical quality of the lens. One solution discovered by the applicants and disclosed herein is to position or embed the composite material within or along the haptic chamber walls. More specifically, the solution discovered by the applicants is to position or embed the composite material along or within the radially inner wall of the haptic(s).

Figure 10:
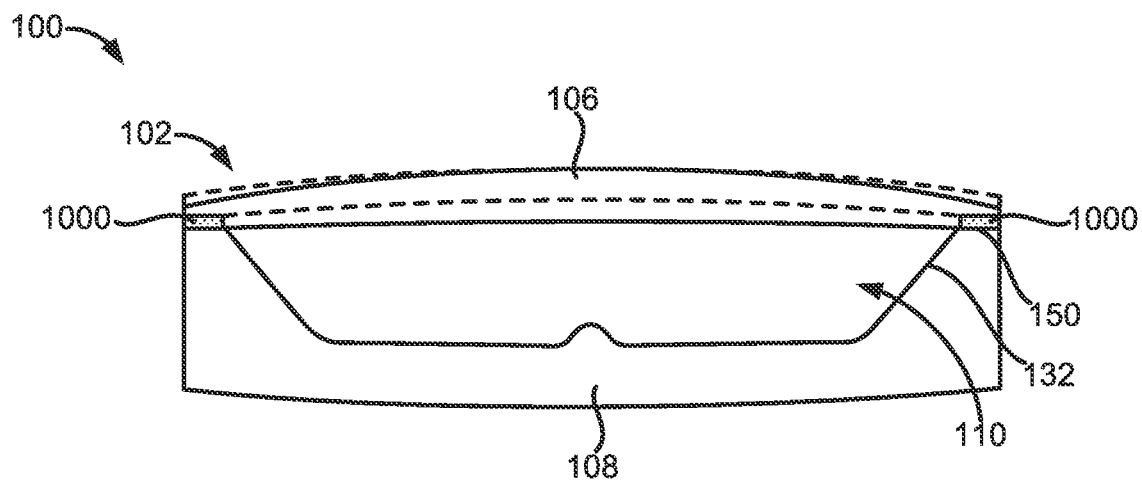
FIG. 10 illustrates a sectional view of an optic portion of another embodiment of the adjustable accommodating intraocular lens comprising an adhesive layer made in part of the composite material.

FIG. 10 illustrates a sectional view of an optic portion 102 of another embodiment of the adjustable AIOL 100 comprising an adhesive layer 1000 made in part of the composite material 200. In some embodiments, the adhesive layer 1000 can comprise the composite material 200 integrated or mixed with the adhesives 148 previously discussed. In other embodiments, the composite material 200 can be positioned or sandwiched in between layers of the adhesive 148.

The adhesive layer 1000 can be positioned or disposed along the peripheral edge 150 of the posterior element 108 (i.e., the top of the raised inner surface 132). Although FIG. 10 illustrates the adhesive layer 1000 as being located along opposing sides of the optic portion 102, it should be understood by one of ordinary skill in the art that the adhesive layer 1000 extends circumferentially around the entire periphery of the optic portion 102. The adhesive layer 1000 can also be referred to as rotationally symmetric.

In some embodiments, the base power of the adjustable AIOL 100 can be configured to decrease in response to an external energy 302 directed or otherwise applied at the adhesive layer 1000. The adhesive layer 10000 can be configured to expand in response to the external energy 302 directed at the adhesive layer 1000. The external energy 302 can be directed at the entire adhesive layer 1000 surrounding the periphery of the optic portion 102.

Expansion of the adhesive layer 1000 can raise the anterior element 106 and increase the volume of the optic fluid chamber 110. This can cause the anterior element 106 to flatten slightly as the internal fluid pressure within the fluid-filled optic fluid chamber 110 decreases.

In some embodiments, bursts or pulses of external energy 302 (e.g., light energy) directed at the adhesive layer 1000 can result in a decrease in base power of the adjustable AIOL 100 by between about −0.10 D and −0.20 D (e.g., about −0.125 D). For example, pulses of green laser light directed at the adhesive layer 1000 can result in a decrease in the base power of the adjustable AIOL 100 by between about −0.10 D and −0.20 D (e.g., about −0.125 D). In some embodiments, the base power of the adjustable AIOL 100 can decrease between about −1.0 D to about −5.0 D (e.g., about −2.0 D) in total in response to bursts or pulses of the external energy 302 directed at the adhesive layer 1000.

Figure 11:
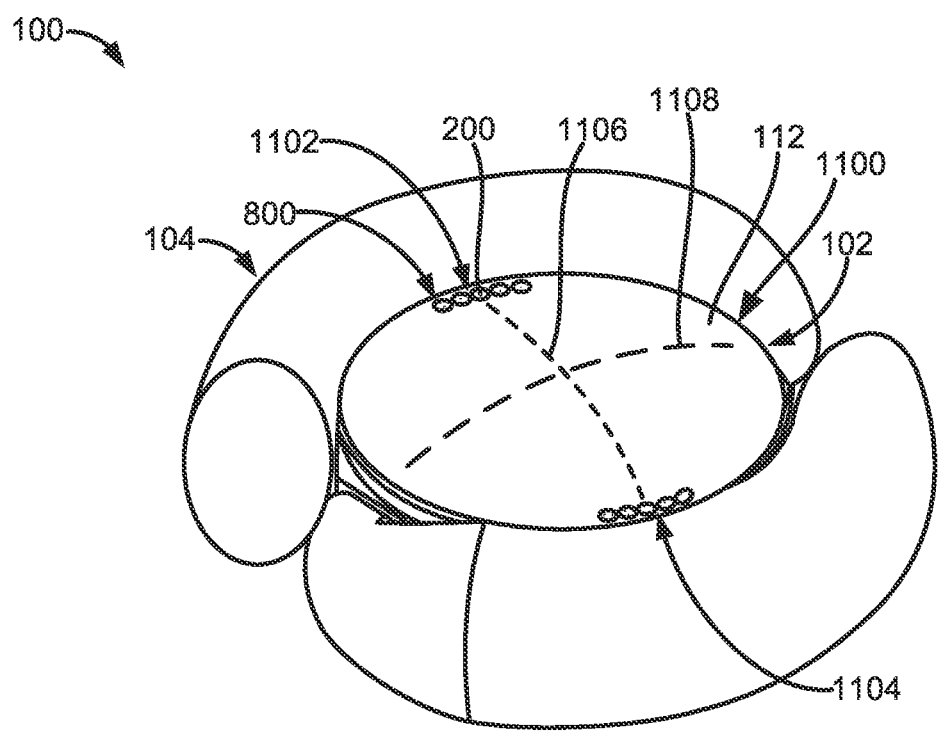
FIG. 11 illustrates a perspective view of another embodiment of the adjustable accommodating intraocular lens configured to exhibit cylindricity in response to an external energy directed at the adjustable accommodating intraocular lens.

FIG. 11 illustrates a perspective view of another embodiment of the adjustable AIOL 100 comprising an adjustable anterior element 1100 having the composite material 200 located or positioned along diametrically opposed peripheral portions of the anterior element 1100. As shown in FIG. 11, the composite material 200 can be shaped or configured as a number of discrete components 800 arranged on opposing peripheral edges of the anterior element 1100.

For example, the composite material 200 can be shaped or configured as a plurality of discrete components 800 lined up along a first peripheral edge 1102 and a second peripheral edge 1104 of the anterior element 1100. The first peripheral edge 1102 can be located diametrically opposed to or separated by about 180 degrees from the second peripheral edge 1104. In all such embodiments, the composite material 200 does not extend along the entire circumference or surround the entire periphery of the anterior element 1100.

In some embodiments, the composite material 200 can be located or adhered in between the anterior optical surface 112 and the anterior inner surface 114. In other embodiments, the composite material 200 can extend out or protrude partly from the anterior optical surface 112. The composite material 200 can be visually perceptible to a clinician or another medical professional when the adjustable AIOL 100 is implanted within an eye of a patient. For example, the composite material 200 can be made in part of an energy absorbing constituent 204 or colorant having or exhibiting a color (e.g., red-color or black-color) that is visually perceptible to the clinician or another medical professional.

The clinician or another medical professional can direct or otherwise apply an external energy 302 to the composite material 200 (for example, to all of the composite material 200 shaped or configured as discrete components 800 along the first peripheral edge 1102 and the second peripheral edge 1104). The composite material 200 can expand in response to this application of external energy 302. This expansion or swelling of the composite material 200 can cause the anterior optical surface 112 of the anterior element 1100 to flatten or exhibit a flatter curvature along a first meridian (referred to as a flat meridian 1106) of the anterior element 1100. The flat meridian 1106 can be substantially perpendicular to another meridian (referred to as a steep meridian 1108) of the anterior element 1100 where the curvature of the anterior element 1100 along this other meridian is substantially unaffected by the expansion of the composite material 200. In this manner, a cylinder or cylindricity is induced on the anterior optical surface 112 of the anterior element 1100. This change in the cylindricity of the anterior element 1100 can persist or remain substantially permanent even after the external energy 302 is no longer directed or applied to the anterior element 1100.

More specifically, in response to the application of the external energy 302, the radius of curvature of the anterior optical surface 112 measured along the flat meridian 1106 can be greater than the radius of curvature of the anterior optical surface 112 measured along the steep meridian 1108. Moreover, in response to the application of the external energy 302, a peripheral thickness of the anterior element 1100 along the flat meridian 1106 can be greater than a peripheral thickness of the anterior element 1100 along the steep meridian 1108.

In some embodiments, applying or directing the external energy 302 at the composite material 200 can induce the anterior element 1100 to have a cylinder power between about +0.50 D to about +5.0 D (e.g., about +1.50 D or about +3.0 D). The cylinder power can be measured along the steep meridian 1108 of the anterior element 1100.

Although FIG. 11 illustrates an adjustable AIOL 100 comprising an adjustable anterior element 1100 having the composite material 200, it is contemplated by this disclosure that the adjustable AIOL 100 can also comprise an adjustable posterior element having the composite material 200. For example, the composite material 200 can be located or positioned along diametrically opposed peripheral portions of the posterior element. The composite material 200 can be shaped or configured as a number of discrete components 800 arranged on opposing peripheral edges of the posterior element.

In some embodiments, the composite material 200 can be located or adhered in between the posterior optical surface 116 and the posterior inner surface 118 (see, for example, FIGS. 1B and 1C). In other embodiments, the composite material 200 can extend out or protrude partly from the posterior optical surface 116. The composite material 200 can be visually perceptible to a clinician or another medical professional when the adjustable AIOL 100 is implanted within an eye of a patient.

The clinician or another medical professional can direct or otherwise apply an external energy 302 to the composite material 200 making up part of the peripheral edges of the posterior element. The composite material 200 can expand in response to this application of external energy 302. This expansion or swelling of the composite material 200 can cause the posterior optical surface 116 to flatten or exhibit a flatter curvature along a flat meridian of the posterior element. The flat meridian can be substantially perpendicular to a steep meridian of the posterior element where the curvature of the posterior element along the steep meridian is substantially unaffected by the expansion of the composite material 200. In this manner, a cylinder or cylindricity is induced on the posterior optical surface 116 of the posterior element. This change in the cylindricity of the posterior element can persist or remain substantially permanent even after the external energy 302 is no longer directed or applied to the posterior element.

More specifically, in response to the application of the external energy 302, the radius of curvature of the posterior optical surface 116 measured along the flat meridian can be greater than the radius of curvature of the posterior optical surface 116 measured along the steep meridian. Moreover, in response to the application of the external energy 302, a peripheral thickness of the posterior element along the flat meridian can be greater than a peripheral thickness of the posterior element along the steep meridian.

In some embodiments, applying or directing the external energy 302 at the composite material 200 can induce the posterior element to have a cylinder power between about +0.5 D to about +5.0 D (e.g., about +1.5 D or about +3.0 D). The cylinder power can be measured along the steep meridian of the posterior element.

One technical problem faced by the applicants is how to induce cylindricity or cylinder in an accommodating intraocular lens without interfering with the optical quality of the lens. One solution discovered by the applicants and disclosed herein is to position or embed the composite material along or within the peripheral edges of an optical element (e.g., the anterior element, the posterior element, or a combination thereof). More specifically, the solution discovered by the applicants is to position or embed the composite material along or within part of two diametrically opposed peripheral edges of at least one of the anterior element and the posterior element.

A number of embodiments have been described. Nevertheless, it will be understood by one of ordinary skill in the art that various changes and modifications can be made to this disclosure without departing from the spirit and scope of the embodiments. Elements of systems, devices, apparatus, and methods shown with any embodiment are exemplary for the specific embodiment and can be used in combination or otherwise on other embodiments within this disclosure. For example, the steps of any methods depicted in the figures or described in this disclosure do not require the particular order or sequential order shown or described to achieve the desired results. In addition, other steps operations may be provided, or steps or operations may be eliminated or omitted from the described methods or processes to achieve the desired results. Moreover, any components or parts of any apparatus or systems described in this disclosure or depicted in the figures may be removed, eliminated, or omitted to achieve the desired results. In addition, certain components or parts of the systems, devices, or apparatus shown or described herein have been omitted for the sake of succinctness and clarity.

Accordingly, other embodiments are within the scope of the following claims and the specification and/or drawings may be regarded in an illustrative rather than a restrictive sense.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. Moreover, additional steps or operations may be provided or steps or operations may be eliminated to achieve the desired result.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein. For example, a description of a range from 1 to 5 should be considered to have disclosed subranges such as from 1 to 3, from 1 to 4, from 2 to 4, from 2 to 5, from 3 to 5, etc. as well as individual numbers within that range, for example 1.5, 2.5, etc. and any whole or partial increments therebetween.

All existing subject matter mentioned herein (e.g., publications, patents, patent applications) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

Reference to the phrase "at least one of", when such phrase modifies a plurality of items or components (or an enumerated list of items or components) means any combination of one or more of those items or components. For example, the phrase "at least one of A, B, and C" means: (i) A; (ii) B; (iii) C; (iv) A, B, and C; (v) A and B; (vi) B and C; or (vii) A and C.

In understanding the scope of the present disclosure, the term "comprising" and its derivatives, as used herein, are intended to be open-ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" "element," or "component" when used in the singular can have the dual meaning of a single part or a plurality of parts. As used herein, the following directional terms "forward, rearward, above, downward, vertical, horizontal, below, transverse, laterally, and vertically" as well as any other similar directional terms refer to those positions of a device or piece of equipment or those directions of the device or piece of equipment being translated or moved.

Finally, terms of degree such as "substantially", "about" and "approximately" as used herein mean the specified value or the specified value and a reasonable amount of deviation from the specified value (e.g., a deviation of up to ±0.1%, ±1%, ±5%, or ±10%, as such variations are appropriate) such that the end result is not significantly or materially changed. For example, "about 1.0 cm" can be interpreted to mean "1.0 cm" or between "0.9 cm and 1.1 cm." When terms of degree such as "about" or "approximately" are used to refer to numbers or values that are part of a range, the term can be used to modify both the minimum and maximum numbers or values.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure.

We claim:

1. A method of adjusting an accommodating intraocular lens, comprising:
    adjusting a base power of the accommodating intraocular lens by directing an external energy at a composite material within at least one of an optic portion and a peripheral portion of the accommodating intraocular lens,
    wherein the composite material comprises an energy absorbing constituent and a plurality of expandable components,
    wherein the optic portion comprises a fluid-filled optic fluid chamber and the peripheral portion comprises at least one haptic comprising a fluid-filled haptic fluid chamber in fluid communication with the optic fluid chamber, wherein the method further comprises directing the external energy at the composite material to displace fluid between the optic fluid chamber and the haptic fluid chamber,
    wherein the optic portion is configured to deform, flex, or change shape in response to fluid entering or exiting the optic fluid chamber, and
    wherein the plurality of expandable components are expandable microspheres, wherein each of the expandable microspheres comprises a blowing agent contained within a thermoplastic shell.

2. The method of claim 1, further comprising adjusting the base power of the accommodating intraocular lens when the accommodating intraocular lens is implanted within an eye of a subject.

3. The method of claim 1, further comprising adjusting the cylindricity of an optical surface of the optic portion of the accommodating intraocular lens by directing an external energy at the composite material arranged at diametrically opposed peripheral edges of the optic portion.

4. The method of claim 1, wherein the external energy is a laser light having a wavelength between about 488 nm to about 650 nm.

5. The method of claim 1, further comprising adjusting the base power of the optic portion between about +0.05 D to about +0.5 D by directing pulses of the external energy at the composite material.

6. The method of claim 1, further comprising adjusting the base power of the accommodating intraocular lens by directing the external energy at the composite material to change a volume of the haptic fluid chamber.

7. The method of claim 1, further comprising adjusting the base power of the accommodating intraocular lens by directing the external energy at the composite material to change a volume of the optic fluid chamber.

8. The method of claim 1, wherein a volume of at least one of the expandable components is configured to expand between about 10× to 50× in response to the external energy directed at the composite material.

9. The method of claim 1, wherein the expandable components comprise between about 5% to about 15% by weight of the composite material.

10. The method of claim 1, wherein the expandable components comprise about 10% by weight of the composite material.

11. The method of claim 1, wherein the energy absorbing constituent is an energy absorbing colorant.

12. The method of claim 11, wherein the energy absorbing colorant is a dye.

13. The method of claim 11, wherein the energy absorbing colorant is a pigment.

14. The method of claim 1, wherein the energy absorbing constituent comprises between about 0.025% to about 1.00% by weight of the composite material.

15. The method of claim 1, wherein at least one of the optic portion and the peripheral portion is made in part of a cross-linked copolymer comprising a copolymer blend, and wherein the composite material is made in part of the copolymer blend.

16. The method of claim 15, wherein the composite material further comprises at least one of reactive acrylic monomer diluents, a photoinitiator, and a thermal initiator.

* * * * *